(12) United States Patent
Liphardt et al.

(10) Patent No.: US 9,921,395 B1
(45) Date of Patent: Mar. 20, 2018

(54) BEAM FOCUSING AND BEAM COLLECTING OPTICS WITH WAVELENGTH DEPENDENT FILTER ELEMENT ADJUSTMENT OF BEAM AREA

(71) Applicant: J.A. WOOLLAM CO., INC, Lincoln, NE (US)

(72) Inventors: Martin M. Liphardt, Lincoln, NE (US); Jeffrey S. Hale, Lincoln, NE (US); Ping He, Lincoln, NE (US); Galen L. Pfeiffer, Roca, NE (US)

(73) Assignee: J.A. WOOLLAM CO., INC., Lincoln, NE (US)

( * ) Notice: Subject to any disclaimer, the term of this patent is extended or adjusted under 35 U.S.C. 154(b) by 5 days.

(21) Appl. No.: 15/530,014

(22) Filed: Nov. 18, 2016

Related U.S. Application Data

(63) Continuation-in-part of application No. 15/330,106, filed on Aug. 8, 2016, now Pat. No. 9,500,843, and a continuation-in-part of application No. 14/545,713, filed on Jun. 9, 2015.

(51) Int. Cl.
  *G02B 17/06* (2006.01)
  *G02B 27/00* (2006.01)
  *G01N 21/21* (2006.01)

(52) U.S. Cl.
  CPC ....... *G02B 17/0663* (2013.01); *G01N 21/211* (2013.01); *G02B 27/0012* (2013.01); *G01N 2021/213* (2013.01); *G01N 2201/0636* (2013.01)

(58) Field of Classification Search
  CPC .............................. G01N 21/21; G01J 1/0411
  USPC ......................................................... 356/369
  See application file for complete search history.

(56) References Cited

U.S. PATENT DOCUMENTS

| | | | |
|---|---|---|---|
| 4,650,279 A | 3/1987 | Magee | 385/116 |
| 4,790,659 A | 12/1988 | Erman et al. | 356/369 |
| 4,832,464 A | 5/1989 | Kato et al. | 359/19 |
| 5,048,970 A | 9/1991 | Milosevic et al. | 356/445 |
| 5,336,885 A | 8/1994 | Rose et al. | 250/305 |
| 5,608,526 A | 3/1997 | Piwonka-Corle et al. | 356/369 |
| 5,798,837 A | 8/1998 | Aspnes et al. | 356/369 |
| 5,859,424 A | 1/1999 | Norton | 250/226 |
| 5,889,593 A | 3/1999 | Bareket | 356/445 |
| 5,917,594 A | 6/1999 | Norton | 356/327 |
| 5,969,818 A | 10/1999 | Johs | G01J 3/447 356/364 |
| 6,227,938 B1 | 5/2001 | Cheetham et al. | 451/6 |
| 6,449,028 B1 | 9/2002 | Grupp et al. | 349/191 |

(Continued)

*Primary Examiner* — Roy M Punnoose
(74) *Attorney, Agent, or Firm* — James D. Welch

(57) ABSTRACT

A reflective optics system that requires the presence of both convex and a concave mirrors that have beam reflecting surfaces. Application thereof achieves focusing of a beam of electromagnetic radiation with minimized effects on a polarization state of an input beam state of polarization that results from adjustment of angles of incidence and reflections from the various mirrors involved. This invention is also a combination of a focusing element and a filtering element that provides an optimum electromagnetic beam cross-sectional area based on optimizing the beam cross-sectional area in view of conflicting effects of aberration and diffraction inherent in said focusing element, which, for each wavelength, vary oppositely to one another with electromagnetic beam cross-sectional area.

38 Claims, 12 Drawing Sheets

(56) References Cited

U.S. PATENT DOCUMENTS

| | | | |
|---|---|---|---|
| 6,549,282 B1 | 4/2003 | Johs et al. | 356/369 |
| 6,600,560 B2 | 7/2003 | Mikkelsen et al. | 356/369 |
| 6,636,309 B1 | 10/2003 | Johs et al. | 356/369 |
| 6,734,967 B1 | 5/2004 | Piwonka-Corle et al. | 356/369 |
| 6,738,138 B2 | 5/2004 | Wei | 356/369 |
| 6,795,185 B2 | 9/2004 | Yoshizawa et al. | 356/369 |
| 6,804,004 B1 | 10/2004 | Johs | G01J 3/14 356/369 |
| 6,819,423 B2 | 11/2004 | Stehle et al. | 356/369 |
| 6,824,813 B1 | 11/2004 | Lill et al. | 427/8 |
| 6,829,049 B1 | 12/2004 | Uhrich et al. | 356/369 |
| 6,859,278 B1 | 2/2005 | Johs et al. | 356/369 |
| 6,865,025 B2 | 3/2005 | Kimura | 395/565 |
| 6,916,584 B2 | 7/2005 | Sreenivasan et al. | 430/22 |
| 6,940,595 B1 | 9/2005 | Johs et al. | 356/369 |
| 6,943,880 B2 | 9/2005 | Kanzaki et al. | 356/369 |
| 6,994,808 B2 | 2/2006 | Lee et al. | 264/121 |
| 7,027,156 B2 | 4/2006 | Watts et al. | 356/401 |
| 7,050,162 B2 | 5/2006 | Opsal et al. | 356/237.1 |
| 7,070,405 B2 | 7/2006 | Sreenivasan et al. | 425/174.4 |
| 7,095,498 B2 | 8/2006 | Horie | 356/369 |
| 7,130,039 B2 | 10/2006 | Vaez-Iravani et al. | 356/237.5 |
| 7,145,654 B2 | 12/2006 | Norton | 356/369 |
| 7,158,231 B1 | 1/2007 | Woollam et al. | 356/369 |
| 7,184,145 B2 | 2/2007 | Amary et al. | 356/369 |
| 7,190,525 B2 | 3/2007 | Ito et al. | 359/599 |
| 7,215,424 B1 | 5/2007 | Liphardt et al. | 356/369 |
| 7,239,391 B2 | 7/2007 | Synowicki et al. | 356/369 |
| 7,248,364 B2 | 7/2007 | Hebert et al. | 356/369 |
| 7,248,420 B2 | 7/2007 | Hayashi et al. | 359/719 |
| 7,251,410 B2 | 7/2007 | Ide | 385/140 |
| 7,265,838 B1 | 9/2007 | Johs et al. | 356/369 |
| 7,274,472 B2 | 9/2007 | Bischoff | 356/635 |
| 7,277,171 B1 | 10/2007 | Johs et al. | 356/369 |
| 7,281,921 B2 | 10/2007 | Watts et al. | 425/385 |
| 7,289,219 B2 | 10/2007 | Norton et al. | 356/445 |
| 7,295,313 B1 | 11/2007 | Johs et al. | 356/369 |
| 7,336,361 B1 | 2/2008 | Liphardt et al. | 356/369 |
| 7,359,052 B2 | 4/2008 | Fielden et al. | 356/369 |
| 7,369,233 B2 | 5/2008 | Nikoonahad et al. | 356/369 |
| 7,495,762 B2 | 2/2009 | Wang et al. | 356/328 |
| 7,505,133 B1 | 3/2009 | Zawaideh et al. | 356/369 |
| 7,505,134 B1 | 3/2009 | Johs et al. | 356/369 |
| 7,616,319 B1 | 11/2009 | Woollam et al. | 356/451 |
| 7,633,625 B1 | 12/2009 | Woollam et al. | 356/451 |
| 7,746,472 B1 | 1/2010 | Johs et al. | 356/369 |
| 7,746,471 B1 | 6/2010 | Johs et al. | 356/369 |
| 7,860,040 B2 | 12/2010 | Thill et al. | 370/314 |
| 8,030,632 B2 | 10/2011 | Norton et al. | 250/559.08 |
| 8,351,036 B1 | 1/2013 | Liphardt | 356/369 |
| 8,749,785 B2 | 6/2014 | Liphardt | 356/369 |
| 8,767,209 B2 | 7/2014 | Li et al. | 356/369 |
| 9,442,016 B2 * | 9/2016 | Liphardt | G01J 1/0411 |
| 9,500,843 B1 * | 11/2016 | Liphardt | G01J 1/0411 |
| 2004/0032664 A1 | 2/2004 | Miller et al. | |
| 2004/0085882 A1 | 5/2004 | Yamamoto et al. | 369/94 |
| 2005/0247866 A1 | 11/2005 | Plewa et al. | |
| 2006/0164734 A1 | 7/2006 | Hayashi et al. | |
| 2009/0108190 A1 | 4/2009 | Plewa et al. | |
| 2009/0322928 A1 | 12/2009 | Robinson et al. | |

* cited by examiner

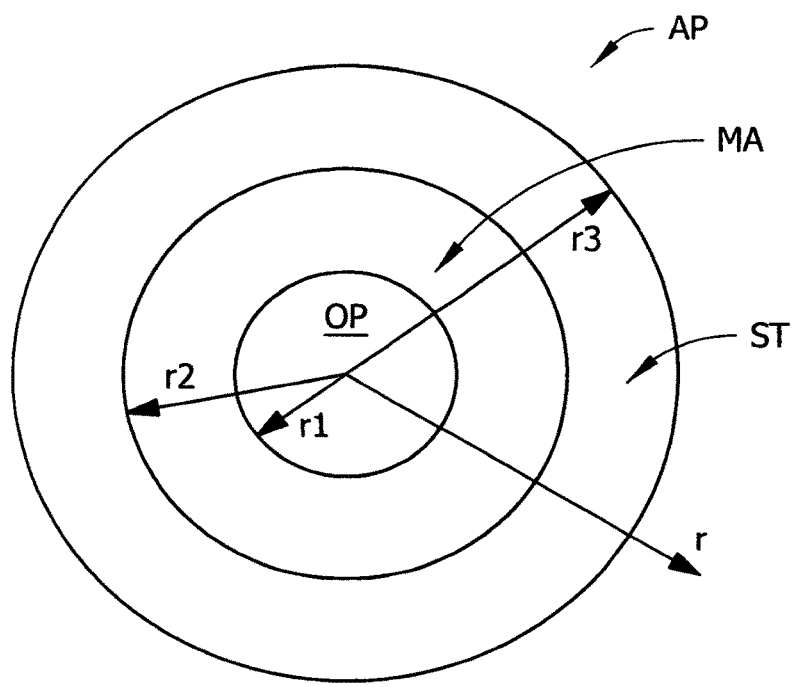
FIG. 3A1
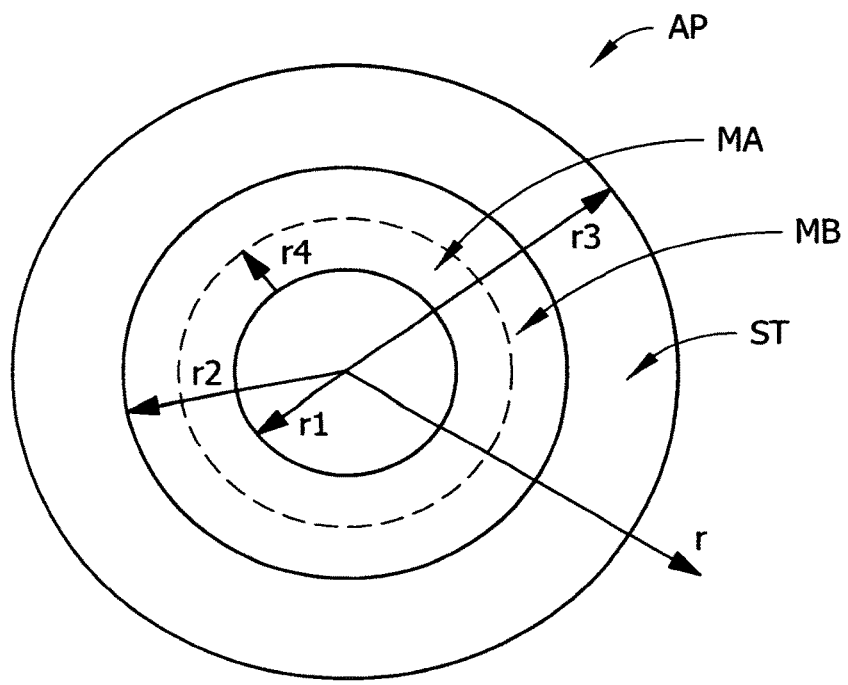
FIG. 3A2

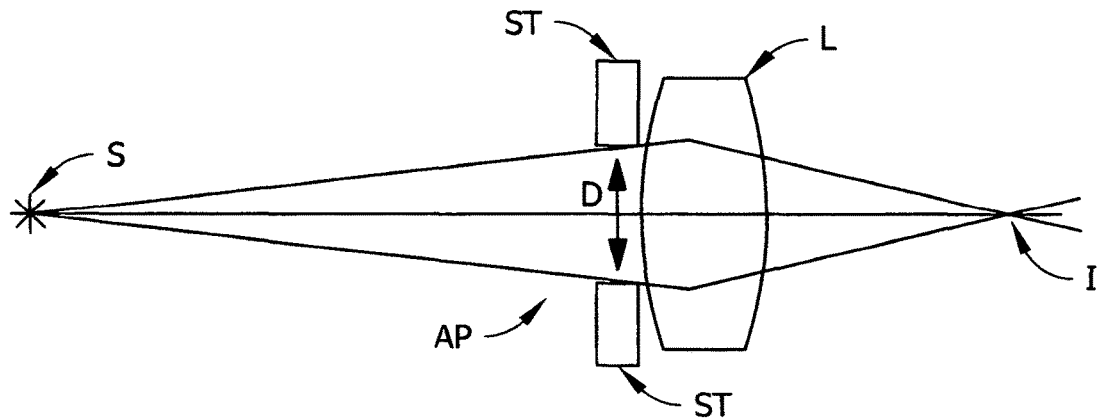
FIG. 4A₁
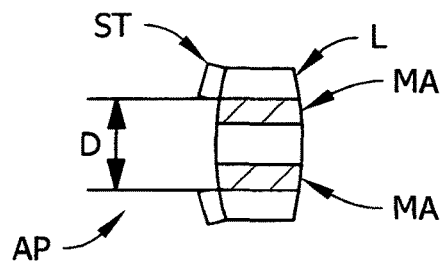
FIG. 4A₂
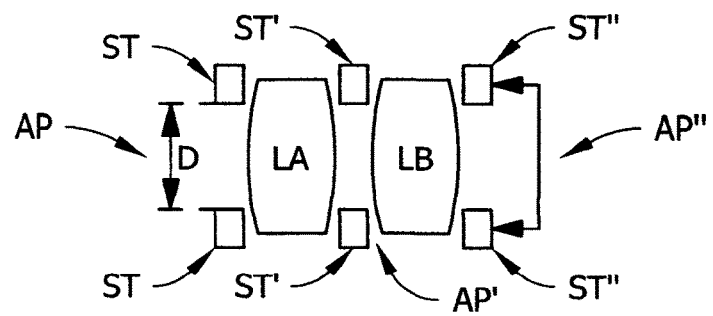
FIG. 4A₃

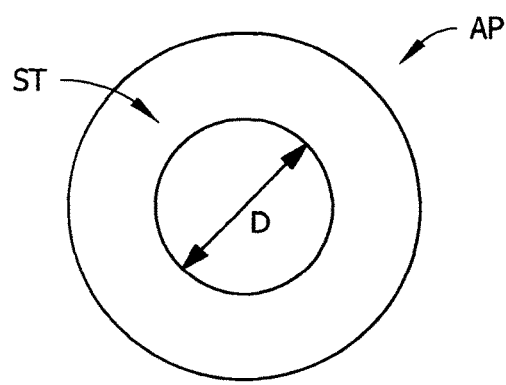
FIG. 4B1
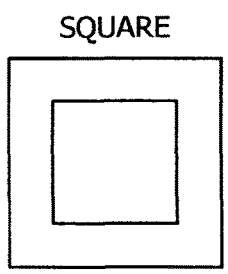
FIG. 4B2
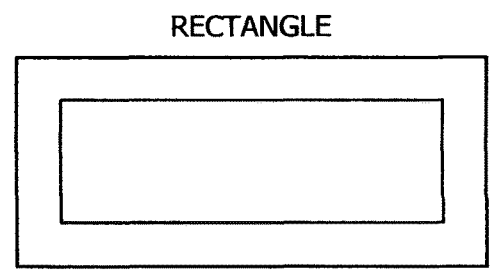
FIG. 4B3
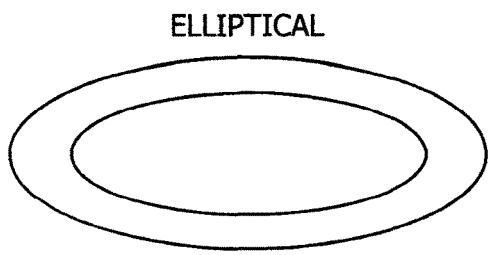
FIG. 4B4
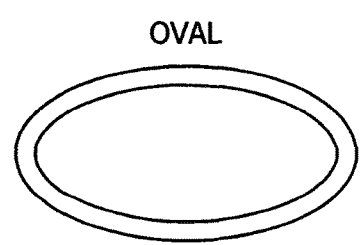
FIG. 4B5

BEAM FOCUSING AND BEAM COLLECTING OPTICS WITH WAVELENGTH DEPENDENT FILTER ELEMENT ADJUSTMENT OF BEAM AREA

This Application is a CIP of application Ser. No. 15/330,106 Filed Aug. 8, 2016, and therevia a Continuation of Ser. No. 14/121,915 Filed Nov. 4, 2014 and therevia Claims Benefit of Provisional Application Ser. No. 61/997,589 Filed Jun. 6, 2014. This Application is also a CIP of application Ser. No. 14/545,713 Filed Jun. 9, 2015.

TECHNICAL FIELD

The present invention relates to focusing beams of electromagnetic radiation onto samples, and more particularly to a reflective optics system that requires the presence of both convex and a concave mirrors that have beam reflecting surfaces. Application thereof achieves focusing of a beam of electromagnetic radiation with minimized effects on a polarization state of an input beam state of polarization that results from adjustment of angles of incidence and reflections from the various mirrors involved. This invention also relates to a system of aperturing a focusing element by use of a filtering element to arrive at an optimum electromagnetic beam cross-sectional area passed by the filtering element, based on optimizing said cross-sectional area in view of conflicting effects of aberration and diffraction inherent in said focusing element, which, for each wavelength, vary oppositely to one another with electromagnetic beam cross-sectional area. More particularly the present invention is a combination of a reflective optics system and a focusing element including a filtering element which can provide neutral density characteristics as a function of wavelength in some wavelengths ranges, and in which the filtering element is not necessarily of uniform optical density and/or thickness.

BACKGROUND

It is known to focus beams of electromagnetic radiation onto samples, such as in the practice of ellipsometry, and said focusing can be achieved using refractive or reflective optics. Numerous Patents provide insight this in general, but a particularly relevant one is U.S. Pat. No. 5,969,818 to Johs et al. This Patent is specifically disclosed as it describes a "Beam Folding Optics", (best shown in FIG. 5 thereof), that comprises four similar mirrors oriented such that reflections from the first and second thereof define a plane of incidence that is substantially orthogonal to a plane of incidence formed by reflections for the third and fourth thereof. The result of applying said Beam directing Optics is to direct a beam of electromagnetic radiation in a desired direction that is other than along a locus of a beam input to said system, but because of polarization state change cancellation effects of reflections from the first two mirrors, and reflections from the last two mirrors, the system has essentially no effect on the polarization state of a beam exiting said Beam Folding Optics, as compared to that of a beam input thereto. Other Patents that describe the "Beam Folding Optics" are: U.S. Pat. Nos. 7,746,472; 7,746,471; 7,633,625; 7,616,319; 7,505,134; 7,336,361; 7,265,838; 7,277,171; 7,265,838; 7,215,424; 7,158,231; 6,859,278; 6,822,738; 6,804,004; and 6,549,282. Another, very recent Patent to Li et al., U.S. Pat. No. 8,767,209, is disclosed as it describes forming angles between incoming and reflected beams of electromagnetic radiation. This is very different from forming angles between planes formed by two sets of incoming and reflected beams, however, as is done in the Present Invention. Additional Patents are further disclosed primarily as they describe beam focusing using mirrors. Said additional Patents are: U.S. Pat. Nos. 4,790,659; 5,048,970; 5,608,526; 5,798,837; 5,917,594; 6,600,560; 6,734,967; 6,795,185; 6,819,423; 6,829,049; 6,943,880; 7,095,498; 7,130,039; 7,184,145; 7,248,364; 7,289,219; 7,359,052; 7,369,233; 7,505,133; 7,860,040 and 8,030,632.

The present invention builds on the insight provided primarily by the 818 patent, but adds focusing capability to the system by providing both convex and concave mirrors in a system that also utilizes the effect of substantially orthogonal planes, but does not require that four primary mirrors involved to be of similar construction.

It is also known that focusing elements, such as refractive lenses and lens systems, cause both diffraction and aberration to occur in a beam of electromagnetic radiation with which is interacts. It is also known that when the effective diameter of a beam of electromagnetic radiation which impinges on a focusing element is adjusted, the effects of diffraction and of aberration are affected oppositely. That is, as the beam cross-sectional area is increased, the effects of diffraction decrease, but the effects of aberration increase. This leads to a realization that, for each wavelength in the beam, there should be a beam cross-sectional area such that the focusing lens performs "optimally". That is, there exists a cross-section area such that increase or decrease in cross-sectional area will cause combined diffraction or aberration to become worse, (ie. cause lens performance to be worse).

It is also well known that attenuation of the intensity of a beam of electomagnetic radiation which is caused to pass through a material is related to the extinction coefficient and thickness of the material via Beer's Law:

$$Io=Ii(e^{-\alpha T}).$$

Therefore, either an increase in the value of extinction coefficient $\alpha$, or a greater thickness (T) of a material, or a combination of both, can cause a greater attenuation of input intensity (Ii) of components of a beam of electomagnetic radiation which passes through a lens. This is to be contrasted with the situation where input Intensity (Ii) is attenuated by reflection or scattering from a surface of an aperture forming material. Further, it is noted that "reflection" implies a specular condition wherein an angle of incidence of an input beam of electromagnetic radiation component is equal to an angle of reflection; whereas "scattering", while still indicating a deflection of a component of an electromagnetic beam away from transmission through a lens, does not have such a limitation on the angle at which a beam component is deflected.

With the present invention in mind a computer search for Patents and Published Applications was conducted. A few references were identified which are interesting as they relate to aberration corrections. For instance, a Patent to Lee et al., U.S. Pat. No. 6,994,808 describes a planar lens which is designed to compensate chromatic aberration. Another Patent to Kimura, U.S. Pat. No. 6,865,025 provides another optical element for application in compensating aberration. And, a Published Patent Application by Miller et al., No. 2004/0032664 describes a color corrected lens. Other Patents and Published Applications identified are:
Published Applications:
  2009/0322928;
  2009/0108190;

2006/0164734;
2005/0247866;
Patents:
U.S. Pat. Nos. 7,495,762; 7,281,921; 7,248,420;
U.S. Pat. Nos. 7,274,472; 7,190,525; 5,336,885;
U.S. Pat. Nos. 7,251,410; 7,070,405; 4,832,464;
U.S. Pat. Nos. 6,824,813; 7,027,156; 4,650,279.
U.S. Pat. Nos. 6,449,028; 6,916,584;
U.S. Pat. Nos. 5,889,593; 6,277,938;

The above cited Patents are not considered to be particularly relevant to a focusing element that optimises its optical response regarding aberration v. diffraction on a per wavelength basis.

Further identified are U.S. Pat. Nos. 8,749,785 and 8,351,036 which while relevant do not focus on application of filter material which operates to control an effective lens diameter in a specified range of wavelengths, but acts as a neutral density outside thereof.

It is also well known that various materials and stacks of materials or the like have different Transmission v. wavelength characteristics. Patents known by the Inventor herein which are relevant are: U.S. Pat. Nos. 7,239,391; 7,295,313; 6,940,595; and 6,636,309. However, while said general knowledge that stacked materials present with specific response to different wavelengths exists, application of the effect as taught in the present Application is not found in the known prior art. This is particularly the case where application of aperturing and focusing of electromagnetic beams by a present invention system for improving the operation of a focusing element as a function of wavelength is applied in an ellipsometer, polarimeter or the like system.

Japanese Patent Application JP 2003-091862 by Kitabayashi, and a Published Application by Yamamoto et al. 2004/0085882 are also identified. The Kibabayashi 501 reference describes processing two laser beams of electromagnetic radiation in a CD-DVD system, said two beam being provided by solid state laser sources. Said two laser beams, however, are elliptical in cross-sectional shape as they exit the sources thereof, which is not optimum for us in CD-DVD systems. Kibabayashi 501 explains that beams of a circular cross-sectional shape are preferable in CD-DVD systems, and the Kibabayashi 501 reference provides a required Prism (3) in its system that is designed to make changes to one of the two beams which is of a specific wavelength, to make it be substantially circular in cross-section. Importantly, nothing in Kibabayashi 501 remotely suggests removing said Prism (3) as to do so would render the Kibabayashi 501 system inoperable, and nothing in the present invention remotely suggests the presence of such a beam shaping element. However, necessary as it is in Kibabayashi 501, said prism (3) does not operate so successfully at a second wavelength, and this is why the Kibabayashi 501 reference provides for its dichroic, (ie. wavelength absorbing), filter (63) to also be present. Said dichroic filter makes the second wavelength beam substantially circular by presenting an essentially elliptical shape filter region therein to the beam. Also importantly, said Kibabayashi 501 dichroic filter (63) is designed to, at said second wavelength, provide a substantially circular beam exiting therefrom which was not fully affected by that Prism therein (3). It's presence does NOT serve to act on a multiplicity of wavelengths without need of additional elements as does the filter in the present invention, as will be discussed in the Disclosure Section of the Specification.

It is also of interest to consider that Kibabayashi 501 inventor could beneficially add the present invention to its system to provide optimized beam diameters at the two wavelengths it uses for CD and DVD operation. However, Kibabayashi 501 does not remotely suggest this at all, as it does not even mention correcting for diffraction of a beam.

Finally, Patents disclosing other approaches, (eg. apodizing filters, spatial filters, graded lens etc.), to improving imaging performance in metrology systems by adjusting the index of lens material index are:
U.S. Pat. No. 3,843,235 to Mino et al.;
U.S. Pat. No. 8,873,054 to Kandel et al.;
U.S. Pat. No. 8,441,639 to Kandel et al.;
U.S. Pat. No. 9,080,971 to Kandel et al.;
U.S. Pat. No. 7,397,557 to Jeong et al.;
U.S. Pat. No. 5,349,592 to Ando
U.S. Pat. No. 5,859,424 to Norton;
U.S. Pat. No. 6,738,138 to Wei;
U.S. Pat. No. 7,145,654 to Norton; and
U.S. Pat. No. 7,050,162 to Opsal et al.;
and Published Application by Sullivan No. 2014/0016125.

Need exists for a system which, in the context of a reflective optics system that requires the presence of both convex and a concave mirrors that have beam reflecting surfaces, provides wavelength specific material response mediated aperturing and focusing of electromagnetic beams, on a wavelength by wavelength basis, to the end that an optimum beam diameter, in view of both diffraction and aberration effects is approached over a range of wavelengths so that the operation of the lens element is improved, and in which a filtering element is also present which is not necessarily of uniform optical density and/or thickness and can demonstrate neutral density characteristics outside the specified range of wavelengths. The combination of a focusing element, and a filtering element can optionally be present in an ellipsometer or polarimeter system.

DISCLOSURE OF THE INVENTION

The present invention is a system for providing a focused beam (FB) of electromagnetic radiation onto a location on a sample (SAM), said system being a reflective optics system (RFO) sequentially comprising first (M1), second (M2), third (M3) and fourth (M4) mirrors, each of said four mirrors (M1) (M2) (M3 (M4) providing reflective surfaces, with said third (M3) and fourth (M4) mirrors providing convex and concave reflective surfaces, respectively.

In use an input beam (IB) of electromagnetic radiation having a specific polarization state is directed toward said first (M1) mirror and reflects from said reflective surface thereof, such that a first plane of incidence (P1) is formed between said incident beam (IB) and said beam which is reflected from said reflective surface of said first (M1) mirror.

And said beam reflected from the reflective surface of said first (M1) mirror is directed toward said second mirror (M2) and reflects from said reflective surface thereof toward said convex third (M3) mirror, from which it reflects at an off-center location thereon toward said concave fourth (M4) mirror, wherefrom it is reflected by the reflective surface thereof toward said sample (SAM) as a focused (FB) outgoing beam (OB); said beam reflected from the reflective surface of said convex third (M3) mirror and that reflected from said reflective surface of said concave fourth (M4) mirror forming a second plane of incidence (P2), said first (P1) and second (P2) planes of incidence being substantially orthogonal to one another.

The effect of said four reflections from said reflective surfaces of said four (M1) (M2) (M3) (M4) mirrors being to substantially minimize the effects of all said reflections on the specific polarization state of said input beam, and to direct said output beam (OB) and provide it as a focused beam (FB) onto said sample (SAM) at the point it impinges thereupon.

Said system further comprising a filtering element (AP) for naturally adjusting the effective cross-sectional area of a transmitted beam of electromagnetic radiation, as a function of wavelength;

said filtering element being present at a location selected from the group consisting of:
  before mirror (M1);
  between mirrors (M1) and (M2);
  after mirror (M2).

The present invention is also an ellipsometer comprising:
a) a source of a beam of electromagnetic radiation;
b) a polarization state generator;
c) a reflective focusing optics system comprising:
  a system for providing a focused beam (FB) of electromagnetic radiation onto a location on a sample (SAM), said system being a reflective optics system (RFO) sequentially comprising first (M1), second (M2), third (M3) and fourth (M4) mirrors, each of said four mirrors (M1) (M2) (M3 (M4) providing reflective surfaces, with said third (M3) and fourth (M4) mirrors providing convex and concave reflective surfaces, respectively;
  such that in use an input beam (IB) of electromagnetic radiation having a specific polarization state is directed toward said first (M1) mirror and reflects from said reflective surface thereof, such that a first plane of incidence (P1) is formed between said incident beam (IB) and said beam which is reflected from said reflective surface of said first (M1) mirror;
  and such that said beam reflected from the reflective surface of said first (M1) mirror is directed toward said second mirror (M2) and reflects from said reflective surface thereof toward said convex third (M3) mirror, from which it reflects at an off-center location thereon toward said concave fourth (M4) mirror, wherefrom it is reflected by the reflective surface thereof toward said sample (SAM) as a focused (FB) outgoing beam (OB); said beam reflected from the reflective surface of said convex third (M3) mirror and that reflected from said reflective surface of said concave fourth (M4) mirror forming a second plane of incidence (P2), said first (P1) and second (P2) planes of incidence being orthogonal to one another;
  the effect of said four reflections from said reflective surfaces of said four (M1) (M2) (M3) (M4) mirrors being to substantially minimize the effects of all said reflections on the specific polarization state of said input beam, and to direct said output beam (OB) and provide it as a focused beam (FB) onto said sample (SAM) at the point it impinges thereupon;
d) a stage (STG) for supporting a sample (SAM); and
e) a polarization state detector (PSD).

Said system further comprises a filtering element (AP) for naturally adjusting the effective cross-sectional area of a transmitted beam of electromagnetic radiation, as a function of wavelength;

said filtering element being present at a location selected from the group consisting of:
  before mirror (M1);
  between mirrors (M1) and (M2);
  after mirror (M2).

It is noted that Parent application Ser. Nos. 14/121,915 and 15/330,106 presented a related invention that comprises a system for providing a focused beam (FB) of electromagnetic radiation onto a location on a sample (SAM), and in particular the present invention is a reflective optics system (RFO) sequentially comprising first (M1), second (M2), third (M3) fourth (M4), fifth (M3') and sixth (M4') mirrors. Each of said four mirrors (M1) (M2) (M3 (M4) provides a reflective surface, with said third (M3) and fourth (M4), and fifth (M3') and Sixth (M4'), mirrors providing convex and concave reflective surfaces, respectively.

In use an input beam (IB) of electromagnetic radiation having a specific polarization state is directed toward said first (M1) mirror and reflects from said reflective surface thereof, such that a first plane of incidence (P1) is formed between said incident beam (IB) and said beam which is reflected from said reflective surface of said first (M1) mirror. The beam reflected from the reflective surface of said first (M1) mirror is directed toward said second mirror (M2) and reflects from said reflective surface thereof toward said convex third (M3) mirror, from which it reflects at an off-center location thereon toward said concave fourth (M4) mirror, wherefrom it is reflected by the reflective surface thereof toward said sample (SAM) as a focused (FB) outgoing beam (OB). Said beam reflected from the reflective surface of said convex third (M3) mirror and that reflected from said reflective surface of said concave fourth (M4) mirror forming a second plane of incidence (P2), said first (P1) and second (P2) planes of incidence being orthogonal to one another.

The effect of said four reflections from said reflective surfaces of said four (M1) (M2) (M3) (M4) mirrors is to substantially minimize the effects of all said reflections on the specific polarization state of said input beam, and to direct said output beam (OB) and provide it as a focused beam (FB) onto said sample (SAM) at the point it impinges thereupon.

Said system can involve the first (M1) and (M2) mirrors both having flat reflecting surfaces, or at least one of the first (M1) and second (M2) mirrors has a non-flat reflecting surface, or both the first (M1) and second (M2) mirrors having non-flat reflecting surfaces.

The input beam (IB), all reflected beams and the output beam (OB) can be monochromatic or spectroscopic.

The first (P1) and second (P2) planes of incidence an be defined by central rays in the reflected beams involved.

The input (IB), and the various reflected and output (OB) beams can each be considered to consist of multiple, (typically at least 16), cross-sectional areas, and in which the calculated overall effect on polarization state of the various reflections from mirrors (M1) (M2) (M3) and (M4) is arrived at by an averaging thereof.

The angles of incidence of the electromagnetic beams approaching said third (M3) and fourth (M4) mirrors can be set to twelve (12) and twenty-four (24) degrees respectively, and the angles of incidence of the electromagnetic beams approaching said first (M1) and second (M2) mirrors can be each selected from the group consisting of:
  a) less than eighteen degrees;
  b) eighteen degrees; and
  c) greater that eighteen degrees.

Of course the recitation of twelve (12) and twenty-four (24) degrees are only relevant examples and other angle combinations can be used, (ie. generalized θ1 and θ2), and the angles of incidence of the electromagnetic beams approaching said first (M1) and second (M2) mirrors can be each selected from the group consisting of:
  a) less than $(\theta 1+\theta 2)/2$;
  b) $(\theta 1+\theta 2)/2$ degrees; and
  c) greater that $(\theta 1+\theta 2)/2$ degrees.

Also presented in Parent application Ser. Nos. 14/121,915 and 15/330,106 was an ellipsometer comprising:
a) a source (S) of a beam of electromagnetic radiation;
b) a polarization state generator (PSG);
c) a reflective focusing optics (RFO) system comprising:
a system for providing a focused beam (FB) of electromagnetic radiation onto a location on a sample (SAM), said system being a reflective optics system (RFO) sequentially comprising first (M1), second (M2), third (M3) and fourth (M4) mirrors, each of said four mirrors (M1) (M2) (M3 (M4) providing reflective surfaces, with said third (M3) and fourth (M4) mirrors providing convex and concave reflective surfaces, respectively.

In use an input beam (IB) of electromagnetic radiation having a specific polarization state is directed toward said first (M1) mirror and reflects from said reflective surface thereof, such that a first plane of incidence (P1) is formed between said incident beam (IB) and said beam which is reflected from said reflective surface of said first (M1) mirror;
and such that said beam reflected from the reflective surface of said first (M1) mirror is directed toward said second mirror (M2) and reflects from said reflective surface thereof toward said convex third (M3) mirror, from which it reflects at an off-center location thereon toward said concave fourth (M4) mirror, wherefrom it is reflected by the reflective surface thereof toward said sample (SAM) as a focused (FB) outgoing beam (OB); said beam reflected from the reflective surface of said convex third (M3) mirror and that reflected from said reflective surface of said concave fourth (M4) mirror forming a second plane of incidence (P2), said first (P1) and second (P2) planes of incidence being orthogonal to one another.

The effect of said four reflections from said reflective surfaces of said four (M1) (M2) (M3) (M4) mirrors is to substantially minimize the effects of all said reflections on the specific polarization state of said input beam, and to direct said output beam (OB) and provide it as a focused beam (FB) onto said sample (SAM) at the point it impinges thereupon.

Said ellipsometer further comprises:
d) a stage (STG) for supporting a sample (SAM); and
e) a polarization state detector (PSD).

Said system can also further comprise additional fifth (M1'), sixth (M2'), seventh (M3') and eighth (M4') mirrors arranged in substantially mirror image locations with respect to mirrors (M1), (M2), (M3) and (M4), about a vertical plane extending from the location on the sample where the electromagnetic beam impinges thereupon, said mirrors (M1'), (M2'), (M3') ad (M4') serving to collimate and direct said beam that reflects from said sample (SAM), into a polarization state detector (PSD).

Said system can also further comprise providing of a computer system (CMP), said computer system (CMP) being programmed with a mathematical model of the system provided in step a) and sample (SAM); such that in use said source (S) of an input beam (IB) of electromagnetic radiation having a specific polarization state is caused to direct an input beam (IB) at at least one angle of incidence and at least one known polarization state, toward said first (M1) mirror, reflect therefrom and interact with said second (M2), third (M3) and forth (M4) mirrors, before reflecting from said sample (SAM) and being directed into said polarization state detector (PSD) via mirrors (M1'), (M2'), (M3') and (M4') and being detected by detector (DET) therewithin; and such that said detector (DET) outputs data into said computer in which a mathematical regression is performed to assign best fit values to parameters in said mathematical model.

Said system can also provide that said mathematical model comprises parameters to account for various selections from at least:
surface reflectivity characteristics of the surfaces of said first (M1), second (M2), third (M3) and forth (M4) mirrors before said sample, including the effects of any thin layers thereon;
surface reflectivity characteristics of the surfaces of said fifth (M1'), sixth (M2'), seventh (M3') and eighth (M4') mirrors after said sample, including the effects of any thin layers thereon;
angles of incidence of said electromagnetic beam with respect to the surfaces of said first (M1), second (M2), third (M3) and forth (M4) fifth (M1'), sixth (M2'), seventh (M3') and eighth (M4') mirrors, at the location thereupon at which it impinges;
sample surface reflectivity characteristics, including the effects of any thin layers thereon;
angle of incidence of said electromagnetic beam to the surface of said sample;
means for spectroscopic averaging to account for the presence of more than one wavelength in said electromagnetic beam;
means to account for electromagnetic beam smearing to account for component deviations from a central beam component;
polarizer, compensator and analyzer effects.

The present invention also includes a method of calibrating an ellipsometer system comprising a focusing optics (RFO) on a source (S) side of a sample (SAM) and a focusing optics (RFO') on a detector (DET) side of said sample (SAM), to provide a system that minimizes the effect of multiple beam reflections therewithin on polarization state, comprising the steps of:
providing a system for providing a focused beam (FB) of electromagnetic radiation onto a location on a sample (SAM), said system being a reflective optics system (RFO) sequentially comprising first (M1), second (M2), third (M3) and fourth (M4) mirrors, each of said four mirrors (M1) (M2) (M3 (M4) providing reflective surfaces, said first (M1) and second (M2) mirrors being selected from the group consisting of:
a) both (M1) and (M2) are flat mirrors;
b) one of (M1) and (M2) is not flat;
c) both (M1) and (M2) are not flat.
Further, and said third (M3) and forth (M4) are selected from the group consisting of:
said third (M3) and fourth (M4) mirrors provide convex and concave reflective surfaces, respectively;
both said third (M3) and fourth (M4) mirrors providing concave reflective surfaces;
one of said third (M3) and forth (M4) mirrors being concave and the other planar
In use an input beam (IB) of electromagnetic radiation having a specific polarization state is directed toward said first (M1) mirror and reflects from said reflective surface thereof, such that a first plane of incidence (P1) is formed between said incident beam (IB) and said beam which is reflected from said reflective surface of said first (M1) mirror; and such that said beam reflected from the reflective surface of said first (M1) mirror is directed toward said second mirror (M2) and reflects from said reflective surface thereof toward said third (M3) mirror, from which it reflects from a location thereon toward said fourth (M4) mirror, wherefrom it is reflected by the reflective surface thereof toward said sample (SAM) as a focused (FB) outgoing beam (OB); said beam reflected from the reflective surface of said third (M3) mirror and impinging on the forth mirror, which beam reflects from said reflective surface of said fourth (M4) mirror forming a second plane of incidence (P2), said first (P1) and second (P2) planes of incidence being substantially orthogonal to one another.

The effect of said four reflections from said reflective surfaces of said four (M1) (M2) (M3) (M4) mirrors is to substantially minimize the effects of all said reflections on the specific polarization state of said input beam, and to direct said output beam (OB) and provide it as a focused beam (FB) onto said sample (SAM) at the point it impinges thereupon;

Said method further comprises providing a sample (SAM) upon which said outgoing beam (OB) impinges in use; and said method further comprises providing additional reflective optics (RFO') in the form of fifth (M1'), sixth (M2'), seventh (M3') and eighth (M4') mirrors arranged in substantially mirror image locations with respect to mirrors (M1), (M2), (M3) and (M4), about a vertical plane extending from the location on the sample where the electromagnetic beam impinges thereupon, said mirrors (M1'), (M2'), (M3') ad (M4') serving to direct said beam that reflects from said sample (SAM), into a polarization state detector (PSD) as collimated, converging or diverging.

In use a beam reflecting from said sample (SAM) reflects from fifth mirror (M1') onto said sixth mirror (M2') from which it reflects onto seventh mirror (M3') toward said eighth mirror (M4') from which it reflects then enters said polarization state detector (PSD) and the multi-element detector thereof, said incident and reflected beams with respect to mirrors (M4') and (M1') forming planes (P1)' and (P2') which are orthogonal to one another.

As regards the present invention, said system for providing a focused beam (FB) of electromagnetic radiation onto a location on a sample (SAM), either alone or in an ellipsometer, further comprises a filtering element (MA) (MB) (ST) for naturally adjusting the effective cross-sectional area of a transmitted beam of electromagnetic radiation, as a function of wavelength;
said filtering element being present at a location selected from the group consisting of:
before mirror (M1);
between mirrors (M1) and (M2);
after mirror (M2).

Said method further comprises providing a computer system (CMP), said computer system (CMP) being programmed with a mathematical model of the system and sample (SAM); and causing said source (S) of an input beam (IB) of electromagnetic radiation having a specific polarization state to direct an input beam (IB) at at least one angle of incidence and at least one known polarization state, toward said first (M1) mirror, reflect therefrom and interact with said second (M2), third (M3) and forth (M4) mirrors, before reflecting from said sample (SAM) and being directed into said polarization state detector (PSD) via mirrors (M1'), (M2'), (M3') and (M4') and being detected by a multi-element detector (DET) therewithin. As a result said multi-element detector (DET) outputs multi-wavelength data into said computer in which a mathematical regression is performed to assign best fit values to parameters in said mathematical model.

And, it is again noted that said mathematical model can comprise parameters to account for various selections from at least:

surface reflectivity characteristics of the surfaces of said first (M1), second (M2), third (M3) and forth (M4) mirrors before said sample, including the effects of any thin layers thereon;

surface reflectivity characteristics of the surfaces of said fifth (M1'), sixth (M2'), seventh (M3') and eighth (M4') mirrors after said sample, including the effects of any thin layers thereon;

angles of incidence of said electromagnetic beam with respect to the surfaces of said first (M1), second (M2), third (M3) and forth (M4) fifth (M1'), sixth (M2'), seventh (M3') and eighth (M4') mirrors, at the location thereupon at which it impinges;

sample surface reflectivity characteristics, including the effects of any thin layers thereon;

angle of incidence of said electromagnetic beam to the surface of said sample;

spectroscopic averaging to account for the presence of more than one wavelength in said electromagnetic beam which enter a detector element;

electromagnetic beam smearing to account for deviations in angle-of-incidence and plane-of-incidence from a central beam component which enters a detector element;

polarizer, compensator and analyzer effects.

It will be appreciated then that the preferred present invention method of calibrating an ellipsometer that comprises reflective optics (RFO) and (RFO'), includes both mechanical adjustments of the various components, and arriving at optimum values for parameters in a mathematical model of the system As it is an important embodiment, it is noted that in the above, mirrors (M3) and (M3') can convex and the beam of electromagnetic radiation reflecting therefrom be from an off-center location thereupon.

The present invention also comprises a system for improving the operation of said system for providing a focused beam (FB) of electromagnetic radiation onto a location on a sample (SAM). As presented in Parent application Ser. No. 14/545,713, said system can be a filtering element (AP) for naturally adjusting the effective cross-sectional area of a transmitted beam of electromagnetic radiation, as a function of wavelength for a multiplicity thereof, placed into the system for providing a focused beam (FB) of electromagnetic radiation onto a location on a sample (SAM).

Said filtering element (AP) for naturally adjusting the effective cross-sectional area of a transmitted beam of electromagnetic radiation, as a function of wavelength for a multiplicity thereof, can be a part of a system that comprises, in either order:
a) a focusing element for focusing an electromagnetic beam, selected from the group consisting of:
a lens; and
a lens system comprising at least two elements; and
b) a filtering element for naturally adjusting the effective cross-sectional area of a transmitted beam of electromagnetic radiation, as a function of wavelength for a multiplicity thereof, said focusing element and said filtering element being functionally associated.

In this case the design criteria of said filtering element is that the effective cross-sectional area of the electromagnetic beam passed by said filtering element to said focusing element is naturally adjusted with respect to wavelength for each wavelength in a range of a multiplicity thereof, such that the performance of the focusing element is rendered approximately optimum in view of an inherent tradeoff between diffraction and aberration effects as a function of electromagnetic beam cross-sectional area. Outside said range of a multiplicity of wavelengths, however, the present invention provides that the filtering element can be neutral density.

The filtering element can absorb electromagnetic radiation of some wavelengths but not others, can reflect electromagnetic radiation of some wavelengths but not others, and/or scatter electromagnetic radiation of some wavelengths but not others.

The filtering element performs at least two selections from the group consisting of:
  it passes;
  it reflects;
  it scatters;
electromagnetic radiation of some wavelengths but not others.

For each wavelength, the focusing element aberration effects increase with the effective cross-sectional area of a beam of electromagnetic radiation directed thereto, and for each wavelength, focusing element diffraction effects decrease with the effective cross-sectional area of a beam of electromagnetic radiation directed thereto.

The effective cross-sectional area of a beam of electromagnetic radiation directed thereto, is naturally adjusted by said filtering element to be approximately optimum based on determining a cross-over point between increasing aberration and decreasing diffraction effects as a function of said cross-sectional area, for at least one wavelength.

The cross-sectional area can be of a shape selected from the group consisting of:
  circular;
  square;
  rectangular;
  oval; and
  elliptical;
wherein progressively greater "effective radii" can be defined, referenced to a common origin. Different materials can be present between adjacently positioned radii.

The focusing element and filtering element can comprise a modular system of lenses and a modular filtering element, or can comprise an integrated system of lenses and filtering element. (That is, when integrated, the filtering element is physically part of the system of lenses).

The focusing element and filtering element can comprise a modular lens system comprising at least two modular lens elements and at least one modular filtering element positioned at a location selected from the group:
  before a lens element;
  after a lens element;
  between said at least two lens elements.

The focusing element and filtering element can comprise a modular lens system comprising at least two modular lens elements and at least one filtering element integrated into at least one of said lens elements at a location selected from the group:
  before said lens element;
  after said lens element.

The focusing element and filtering element can comprise a modular lens system comprising at least two modular lens elements, and at least one filtering element integrated into both lens elements, each thereof being at a location selected from the group:
  before said lens element;
  after said lens element.

The filtering element can be of a constant optical density and/or thickness over its area, or not of a constant over its area, and/or can comprise at least two concentric regions of different materials, wherein a first material is present between a first effective radius and a second greater radius, and a second material is present between said second radius and a third even greater effective radius, all centered about a common origin.

As a relevant application of a present invention system as described above is in ellipsometer and polarimeter or the like systems, it is disclosed that such systems comprise:
  a source of electromagnetic radiation;
  a polarization state generator;
  a stage for supporting a sample;
  a polarization state analyzer; and
  a data detector.
Said ellipsometer, polarimeter or the like system further comprises, at least prior to said stage for supporting a sample
  a system for improving the operation of a focusing element as a function of wavelength, to improve the performance of the focusing element comprising, in either order:
    a) a focusing element for focusing an electromagnetic beam, selected from the group consisting of:
      a lens; and
      a lens system comprising at least two elements; and
    b) a filtering element for naturally adjusting the effective cross-sectional area of a transmitted beam of electromagnetic radiation, as a function of wavelength for a multiplicity thereof;
said focusing element and said filtering element being functionally associated.

The design criteria of said filtering element is that the effective cross-sectional area of the electromagnetic beam passed by said filtering element to said focusing element is naturally adjusted with respect to wavelength for each wavelength in a range of a multiplicity thereof, such that the performance of the focusing element is rendered approximately optimum in view of an inherent tradeoff between diffraction and aberration effects as a function of electromagnetic beam cross-sectional area. Outside said range of a multiplicity of wavelengths, however, the present invention provides that the filtering element can be neutral density.

The filtering element can absorb electromagnetic radiation of some wavelengths but not others.

The filtering element can reflect electromagnetic radiation of some wavelengths but not others.

The filtering element can scatter electromagnetic radiation of some wavelengths but not others.

The filtering element can perform at least two selections from the group consisting of:
  it passes;
  it reflects;
  it scatters;
electromagnetic radiation of some wavelengths but not others, wherein, for each wavelength, focusing element aberration effects increase with the effective cross-sectional area of a beam of electromagnetic radiation directed thereto and wherein for each wavelength, focusing element diffraction effects decrease with the effective cross-sectional area of a beam of electromagnetic radiation directed thereto.

The effective cross-sectional area of a beam of electromagnetic radiation directed thereto, is then naturally adjusted by said filtering element to be approximately optimum based on determining a cross-over point between increasing aberration and decreasing diffraction effects as a function of said cross-sectional area, for at least one wavelength.

The focusing element and filtering element can comprise a modular lens and a modular filtering element.

The focusing element and filtering element can comprise an integrated lens and filtering element.

The focusing element and filtering element can comprise a modular lens system comprising at least two modular lens elements and at least one modular filtering element positioned at a location selected from the group:
- before a lens element;
- after a lens element;
- between said at least two lens elements.

The focusing element and filtering element can comprise a modular lens system comprising at least two modular lens elements and at least one filtering element integrated into at least one of said lens elements at a location selected from the group:
- before said lens element;
- after said lens element.

The focusing element and filtering element can comprise a modular lens system comprising at least two modular lens elements, and at least one filtering element integrated into both lens elements, each thereof being at a location selected from the group:
- before said lens element;
- after said lens element.

The filtering element can be of a constant thickness over its area, or not constant over its area and/or can comprise at least two concentric regions of different materials, wherein a first material is present between a first effective radius and a second greater radius, and a second material is present between said second radius and a third even greater effective radius, all centered about a common origin.

It is mentioned that one way of thinking about the present invention filtering element, is that it is a wavelength dependent system for naturally adjusting a numerical aperture size. And, note that the present invention provides the same filtering characteristics at each radial circumference through a 360 degree rotation about said common origin.

Many of the same features as Claimed herein were originally disclosed in U.S. Pat. No. 8,749,785. However, for Examiner convenience, it is pointed out that an emphasis in the present Claims is that an applied filtering element is not necessarily of uniform optical density and/or thickness, and it can be configured as a selection from the group consisting of:
- optical density and/or thickness is greatest near the center thereof; and
- optical density and/or thickness is smallest near the center thereof.

It is, however, within the scope of the present Claims to provide a system in which the filtering element is of uniform optical density, in at least some regions thereof. It is an important point that while the presently Claimed system can be designed to operate best to control beam diameter in a specified limited range in a range of a multiplicity wavelengths, said system as now disclosed can be operated, in or outside said limited range of wavelengths. Further, and importantly, the presently Claimed system can be designed to be an optical filter that provides neutral density filter characteristics, or has tailored transmissive characteristics for wavelengths outside said limited range of wavelengths in which it operates best. This is considered to be significant in the Presently Claimed invention.

The rational of the present invention is that in ellipsometric applications it is at times convenient to leave the present invention in place during measurements at wavelengths outside the range of wavelengths at which it approximately optimizes beam diameter, and utility arises from tailoring the characteristics thereof in said additional wavelength ranges.

The present invention also is a method of applying a system for improving the operation of a focusing element as a function of wavelength for a multiplicity thereof in a given range thereof comprising:
a) providing a system as described above;
b) applying said system for improving the operation of a focusing element as a function of wavelength for a multiplicity thereof in a given range thereof, at wavelengths outside said given range thereof for which it improves the operation of a focusing element as a function of wavelength for a multiplicity thereof in said given range.

Said method can involve the filtering element not being of uniform optical density, said optical density varying as a selection from the group consisting of: the optical density and/or thickness is greatest near the center thereof; and the optical density and/or thickness is smallest near the center thereof.

Said method as can involve the filtering element acting as a substantially neutral density filter for wavelengths outside said given multiplicity range of wavelengths.

The present invention is most particularly found in a combination of the teachings above, resulting in a system for providing a focused beam (FB) of electromagnetic radiation onto a location on a sample (SAM), said system being a reflective optics system (RFO) sequentially comprising first (M1), second (M2), third (M3) and fourth (M4) mirrors, each of said four mirrors (M1) (M2) (M3 (M4) providing reflective surfaces, with said third (M3) and fourth (M4) mirrors providing convex and concave reflective surfaces, respectively.

In use an input beam (IB) of electromagnetic radiation having a specific polarization state is directed toward said first (M1) mirror and reflects from said reflective surface thereof, such that a first plane of incidence (P1) is formed between said incident beam (IB) and said beam which is reflected from said reflective surface of said first (M1) mirror;
and such that said beam reflected from the reflective surface of said first (M1) mirror is directed toward said second mirror (M2) and reflects from said reflective surface thereof toward said convex third (M3) mirror, from which it reflects at an off-center location thereon toward said concave fourth (M4) mirror, wherefrom it is reflected by the reflective surface thereof toward said sample (SAM) as a focused (FB) outgoing beam (OB); said beam reflected from the reflective surface of said convex third (M3) mirror and that reflected from said reflective surface of said concave fourth (M4) mirror forming a second plane of incidence (P2), said first (P1) and second (P2) planes of incidence being substantially orthogonal to one another.

The effect of said four reflections from said reflective surfaces of said four (M1) (M2) (M3) (M4) mirrors being to substantially minimize the effects of all said reflections on the specific polarization state of said input beam, and to direct said output beam (OB) and provide it as a focused beam (FB) onto said sample (SAM) at the point it impinges thereupon;

Said system further comprises an additional focusing element system that provides operational characteristics which vary radially as a function of wavelength, for a multiplicity thereof, said focusing element system comprising, in either order:

a) a focusing element for focusing an electromagnetic beam, selected from the group consisting of:
   a lens (L); and
   a lens system comprising at least two elements (LA) (LB); and
b) a filtering element (MA) (MB) (ST) for naturally adjusting the effective cross-sectional area of a transmitted beam of electromagnetic radiation, as a function of wavelength;
said focusing element (L) (LA) (LB) and said filtering element (MA) (MB) (ST) being functionally associated.

The design criteria of said filtering element (MA) (MB) (ST) is that the effective cross-sectional area of the electromagnetic beam passed by said filtering element (MA) (MB) (ST) to said focusing element (L) (LA) (LB) is naturally adjusted with respect to wavelength for each wavelength in a range of a multiplicity thereof, such that the performance of the focusing element (L) (LA) (LB) is rendered approximately optimum in view of an inherent tradeoff between diffraction and aberration effects as a function of electromagnetic beam cross-sectional area in said range of a multiplicity of wavelengths;
said additional focusing element system being present at a selection from the group consisting of:
   before mirror (M1);
   between mirrors (M1) and (M2);
   after mirror (M2).

Said system can be present in an Ellipsometer, Polarimeter, spectrophotometer or Reflectometer.

The present invention will be better understood by reference to the Detailed Description Section of this Specification, in combination with the Drawings.

BRIEF DESCRIPTION OF THE DRAWINGS

FIG. 3AB demonstrates typical components of a Polarization State Generator (PSG) as a Polarizer (P), and optionally a Compensator (C).

FIG. 3AC demonstrates typical components of a Polarization State Detector (PSD) as an Analyzer (A), and optionally a Compensator (C) and a multi-element Detector (DET).

FIGS. 3A1 and 3A2 show an aperture which is made from various materials at various radial extents.

FIG. 3B' shows a non-uniform optical density or thickness in filter characteristic in other than optimum wavelength range, when transmission is greatest near the center of the filter.

FIG. 3C' shows an expanded neutral density (NDF) region compared to FIG. 1*c*, indicating benefit can obtain by tailored optical density or thickness outside the optimum wavelength range.

FIG. 4A1 shows a side view of a modular lens (L) with an aperture (AP) placed just therebefore.

FIG. 4A2 shows a side view of an integrated lens (L) and aperture (AP).

FIG. 4A3 a lens (L) can be a lens system comprising a plurality of elements.

FIG. 4B1 shows a front view of a circular lens (L) and aperture (AP).

FIGS. 4B2-4B5 show front views of various alternative lens shapes.

FIG. 5 shows a plot of beam energy as a function of aperture (AP) Radius (r).

DETAILED DESCRIPTION

Figure 1A:
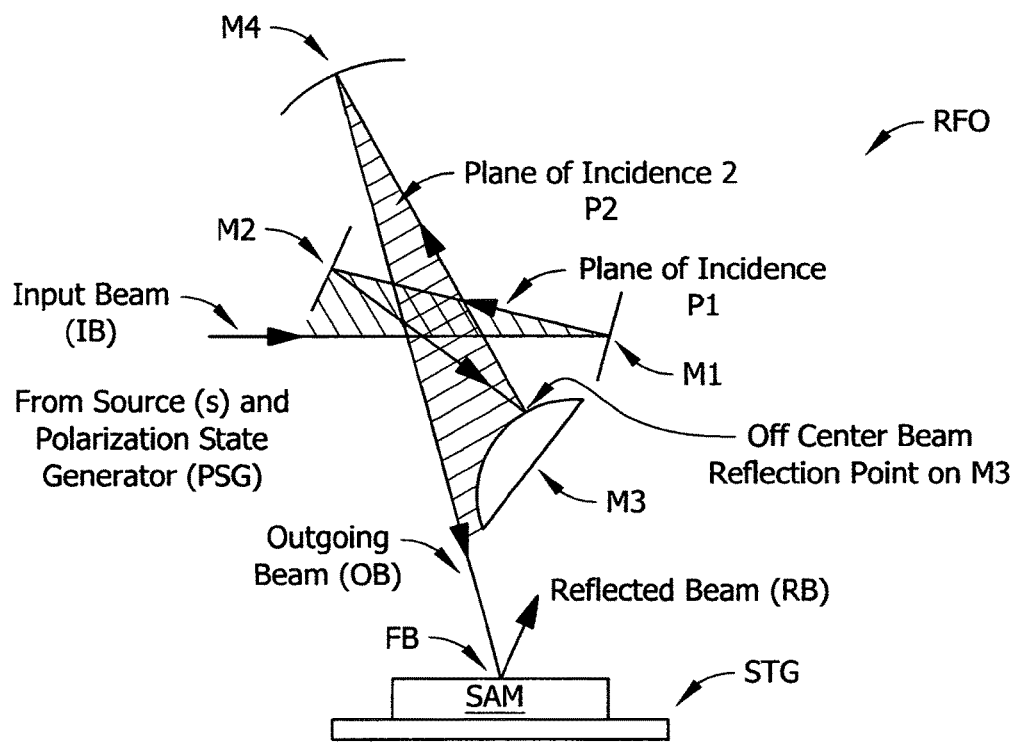
FIG. 1A shows a system for providing a focused beam (FB) of electromagnetic radiation onto a location on a sample (SAM) with minimal change of polarization state therein.

Turning now to FIG. 1A, there is shown a system for providing a focused beam (FB) of electromagnetic radiation onto a location on a sample (SAM), and in particular the present invention is a reflective optics system (RFO) sequentially comprising first (M1), second (M2), third (M3) and fourth (M4) mirrors. Each of said four mirrors (M1) (M2) (M3 (M4) provides reflective surfaces, with said third (M3) and fourth (M4) mirrors providing convex and concave reflective surfaces, respectively.

Shown is an input beam (IB) of electromagnetic radiation, (having a specific polarization state), which is directed toward said first (M1) mirror and reflects from said reflective surface thereof, such that a first plane of incidence (P1) is formed between said incident beam (IB) and said beam which is reflected from said reflective surface of said first (M1) mirror. The beam reflected from the reflective surface of said first (M1) mirror is directed toward said second mirror (M2) and reflects from said reflective surface thereof toward said convex third (M3) mirror, from which it reflects at an off-center location thereon toward said concave fourth (M4) mirror, wherefrom it is reflected by the reflective surface thereof toward said sample (SAM) as a focused (FB) outgoing beam (OB). Said beam reflected from the reflective surface of said convex third (M3) mirror and that reflected from said reflective surface of said concave fourth (M4) mirror forming a second plane of incidence (P2), said first (P1) and second (P2) planes of incidence being orthogonal to one another. It is noted that in use each of said mirrors (M1), (M2), (M3) and (M4) receives a beam approaching it at an angle of incidence to a surface thereof, and in conjunction with a perpendicular to each said mirror at the point where the beam impinges thereupon, a plane of incidence is defined. In a preferred embodiment it happens that the same Planes are defined by paired mirrors (M1) and (M2), (ie. Plane (P1)), and by paired mirrors (M3) and (M4), (ie. Plane (P2)).

The effect of said four reflections from said reflective surfaces of said four (M1) (M2) (M3) (M4) mirrors is to substantially minimize the effects of all said reflections on the specific polarization state of said input beam, and to direct said output beam (OB) and provide it as a focused beam (FB) onto said sample (SAM) at the point it impinges thereupon.

Said system can involve the first (M1) and (M2) mirrors both having flat reflecting surfaces, or at least one of the first (M1) and second (M2) mirrors has a non-flat reflecting surface, or both the first (M1) and second (M2) mirrors having non-flat reflecting surfaces.

Figure 1B:
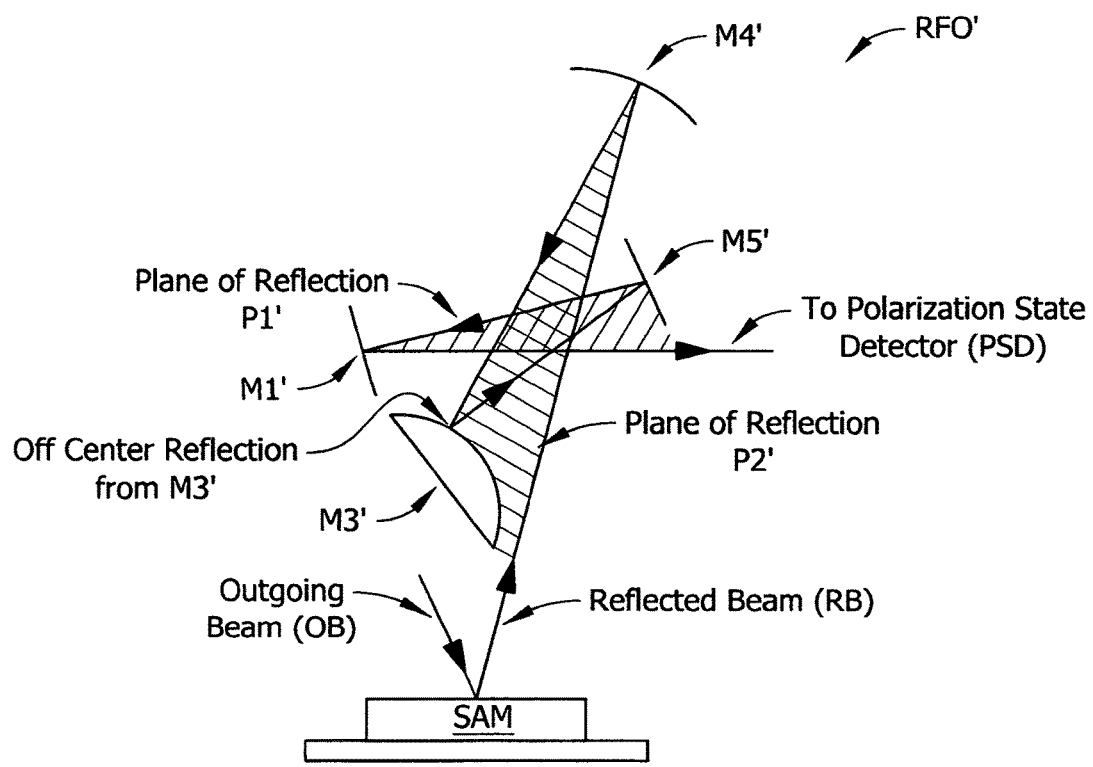
FIG. 1B shows a system for receiving a reflected beam (FB) of electromagnetic radiation a sample (SAM) and directing it toward a Polarization State Detector (PSD).

FIG. 1B shows a system (RFO') for receiving a reflected beam (FB) of electromagnetic radiation a sample (SAM) and directing it toward a Polarization State Detector (PSD) as a collimated beam. Note that FIG. 1B is mirror-image of FIG. 1A as viewed along a vertical line above the location on said Sample (SAM) whereat the Outgoing Beam (OB) impinges thereupon.

Also note that identifiers in FIG. 1B are much the same as in FIG. 1A, with Primes "'" added. That is, for instance, Mirrors (M1), (M2), (M3) and (M4) in FIG. 1a correspond to Mirrors (M1'), (M2'), (M3') and (M4') in FIG. 1b. Also identified in FIG. 1B is a Reflected Beam (RB), which is Output Beam (OB) after it reflects from the Sample (SAM). Note that FIG. 1b Planes (P1') and (P2') are orthogonal, as are Planes (P1) and (P2) in FIG. 1A.

Figure 2A:
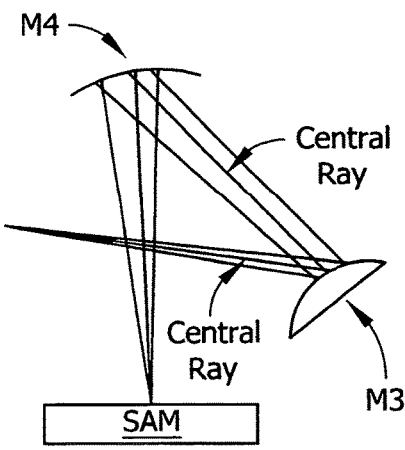
FIG. 2A shows that the off-center reflection from the third convex mirror (M3) provides a "spread-out" beam incident onto the concave fourth (M4) mirror, which fourth (M4) concave mirror serves to focus the spread-out beam onto a sample (SAM) as focused beam (FB).
Figure 2B:
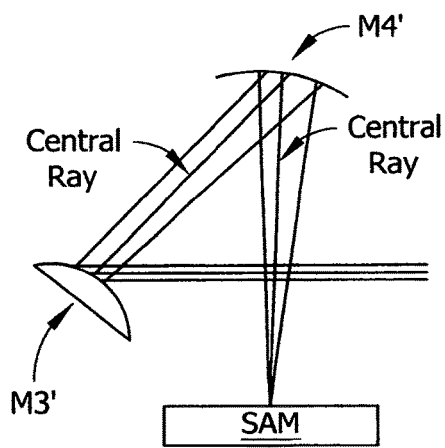
FIG. 2B shows an arrangement for use on the Detector (DET) side of the Sample which compliments that arrangement on the Source (S) side.

FIG. 2A shows that the off-center reflection from the third convex mirror (M3) provides a "spread-out" beam incident onto the concave fourth (M4) mirror, which fourth (M4) concave mirror serves to focus the spread-out beam onto a sample (SAM) as focused beam (FB). FIG. 2B shows an arrangement for use on the Detector (DET) side of the Sample which compliments that FIG. 2a arrangement on the Source (S) side. The presence of Mirrors (M3') and (M4') direct the beam reflecting from the Sample (SAM) into a Detector (DET) in a manner which compliments that used on the Source (S) side via Mirrors (M3) and (M4). (Note that FIGS. 2A and 2B show very small angles of incidence and reflection and are demonstrative of the present invention system geometry, rather than representative of actual angles of incidence and reflection that might be realized in use. Also, FIG. 2B shows a collimated beam exiting Mirror (M3'), however this is not limiting and a converging or diverging beam can also be present. It is to be understood that FIG. 2B, like FIG. 2A is only partial and shown to identify how a beam reflecting from the Sample (SAM) is reflected and sent to the Detector (DET). In use there will be additional mirrors, ((M1') (M2')) present that are like mirrors (M1) and (M2) in FIG. 1B, and there will be planes (P1') and (P2') formed similar to planes (P1) and (P2) between beam reflections from the various mirrors similar to those in FIG. 1A.

Figure 2C:
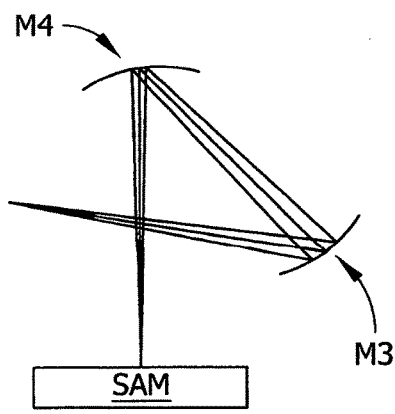
FIGS. 2C and 2D show variations on FIGS. 2A and 2B, but where the convex mirrors (M3) (M3') are replaced with a concave mirrors.
Figure 2D:
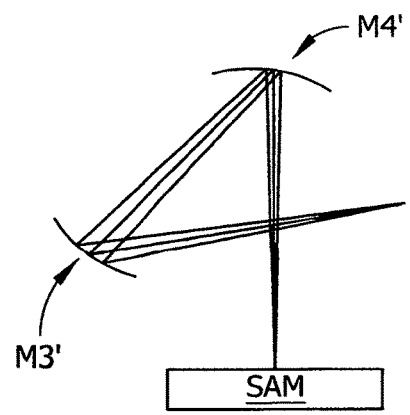
Figure 2E:
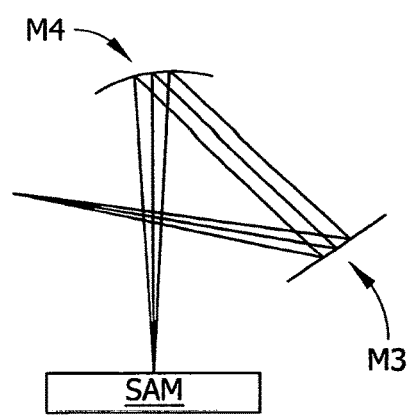
FIGS. 2E and 2F show variations on FIGS. 2A and 2B, but where the convex mirrors (M3) (M3') are replaced with planar mirrors.
Figure 2F:
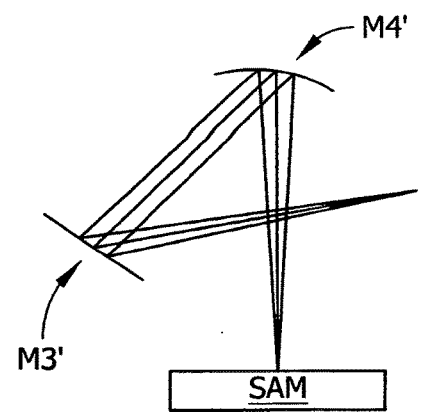
Figure 2G:
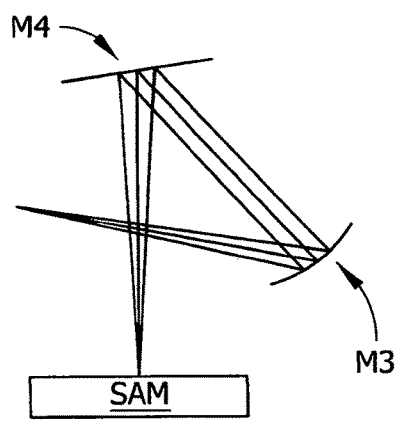
FIGS. 2G and 2H show variations on FIGS. 2A and 2B, but where the convex mirrors (M3) (M3') are replaced with concave mirrors, and concave mirrors (M4) (M4') are replaced with planar mirrors.
Figure 2H:
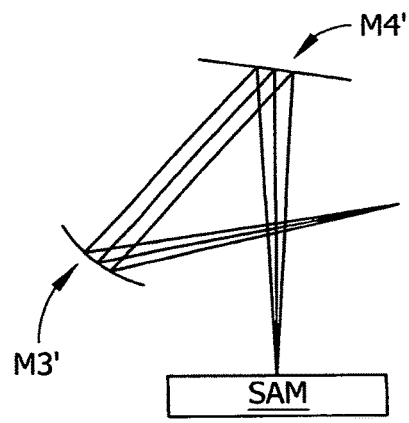

As shown in FIGS. 2A-2H, the Present Invention can comprise a system as in FIGS. 1A and 1B wherein there are, in addition to two planar mirrors, (eg. (M1) (M1') and (M2) (M2') in FIGS. 1A and 1B), there are one convex (M3) and one concave mirror (M4) present, (as per the preferred embodiment), or there are two concave mirrors ((M4) (M4') and (M3) and (M3')) present or wherein there are three planar mirrors (M1) (M1') (M2) (M2') (M3) (M3') present and one concave mirror (M4) (M4'), or three planar mirrors (M1) (M1') (M2) (M2') (M4) (M4') present and one concave mirror (M3) (M3'). In particular, FIGS. 2C and 2D show variations on FIGS. 2A and 2B, but where the convex mirrors (M3) (M3') are replaced with a concave mirrors. FIGS. 2E and 2F show variations on FIGS. 2A and 2B, but where the convex mirrors (M3) (M3') are replaced with planar mirrors. FIGS. 2G and 2H show variations on FIGS. 2A and 2B, but where the convex mirrors (M3) (M3') are replaced with concave mirrors, and concave mirrors (M4) (M4') are replaced with planar mirrors. Note that said system can provide that the reflective properties of each of the mirrors (M1), (M2), (M3) and (M4) are substantially the same, and/or that there are reflective coatings on each of the mirrors (M1), (M2), (M3) and (M4) which are substantially the same based on coating material involved and thickness thereof. While not preferred, these variations are within the scope of the present invention.

Figure 3A:
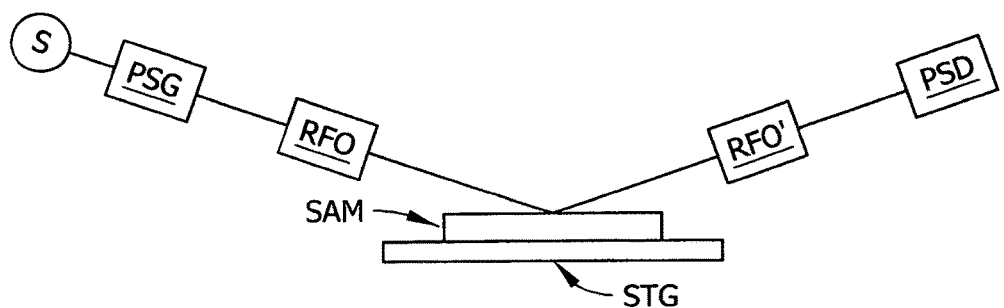
FIG. 3AA shows an ellipsometer system of the present invention which includes the reflective focusing optics (RFO) (RFO').
Figure 3A:
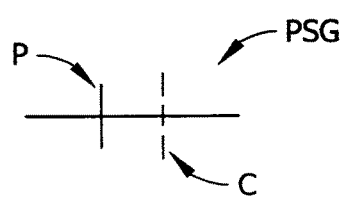
Figure 3A:
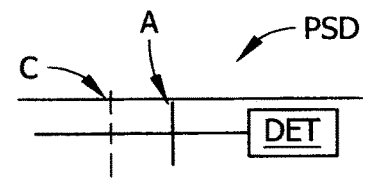

FIG. 3AA shows, in a more straight forward manner, an ellipsometer system of the present invention which includes the present invention reflective focusing optics (RFO) and (RFO'), described above, in conjunction with Polarization State Generator (PSG) and Polarization State Detector (PSD) elements. Note that FIG. 3AB demonstrates the a Polarization State Generator (PSG) typically comprises a Polarizer (P) and can include a Compensator (C). And, FIG. 3AC demonstrates that the (PSD) is to be understood to include a Detector (DET) per se. for use in generating Sample (SAM) describing data from an electromagnetic beam entered thereinto from (RFO'). The (PSD) typically comprises an Analyzer (A), and can include an optional Compensator (C). In general a Polarization State Generator (PSG) comprises a Source (S) of an Input Beam (IB) of electromagnetic radiation and a polarizer, and a Polarization State Detector comprises an Analyzer (A) and multi-element Detector (DET).

It is to be understood that a "central ray" of electromagnetic radiation is the center-most ray in a beam thereof, wherein a beam is beneficially considered as a mathematical ensemble of rays, each being infinitely small. Further "collimation" refers to changing a beam in which rays are converging or diverging to one in which rays are substantially parallel.

Turning now to the Drawings, FIG. 3A1 shows an aperture (AP) which is made from various materials at various radial (r) extents. Radius (r1) identifies a opening through which a electromagnetic radiation of a given wavelength can pass. Radius (r2) shows a region of the aperture, outside the radius (r1), which is made of material (A), and radius (r3) shows a region beyond radius (r2) which is a beam stopper (ST). FIG. 3A2 also shows that the aperture (AP) can comprise additional areas made of various other filtering materials, (eg. (MB) between r1 and r4). Additional concentric rings of different filtering materials can be present and the Drawings are to be considered demonstrative and not limiting. A similar plot results for each wavelength. Further, note that the material present between indicated radii r1 and r2 is the same through said 360 degrees, as is the different material between radii r2 and r4. Support for this is found in the present Application FIGS. 3A1 and 3A2. It is noted that this is very different than than what is disclosed by Kibabayashi 501 FIG. 3 which shows that the dichroic filter thereof has an elliptical shaped filter region in order to shape an elliptical shaped beam to be more circular. There is no similar motivation for such filter design in the present invention. The motivation for the present invention filtering approach is that there is a tradeoff between diffraction and aberration effects as a function of electromagnetic beam cross-sectional area presented to a lens focusing element, and this cross-sectional area tradeoff varies with wavelength. (And further note that Kibabayashi 501 does not even mention beam diffraction). The filtering material, (eg. (MA), (MB), (ST)), in the present invention serves to fashion beam cross-sectional diameter so that, for each wavelength present therewithin, the diameter, and hence cross-sectional beam area, is approximately optimum in view of how a focusing element handles it. In addition, the filtering material in the present Application is defined as not necessarily being of uniform optical density and/or thickness, said optical density and/or thickness varying as a selection from the group consisting of:

optical density and/or thickness is greatest near the center thereof; and optical density and/or thickness is smallest near the center thereof.

Figure 3B:
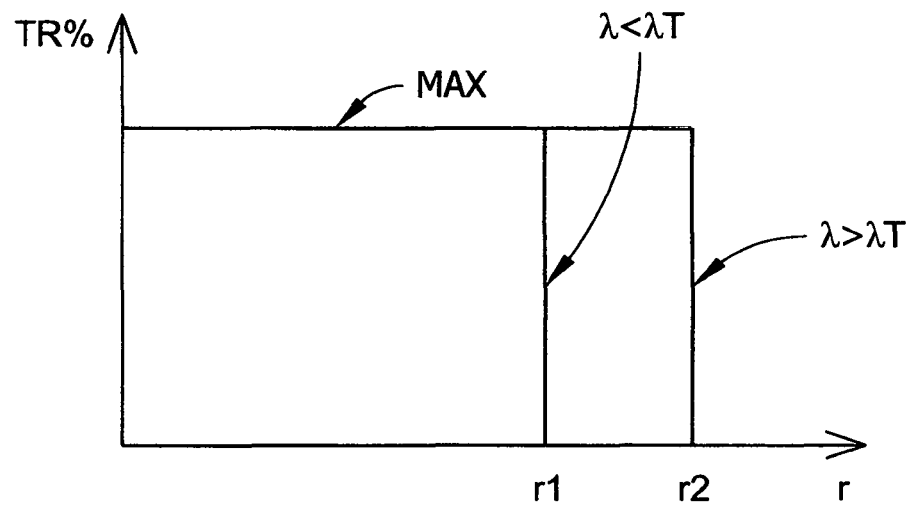
FIG. 3B shows that different wavelengths "see" a different aperture (AP) cross-sectional area.
Figure 3C:
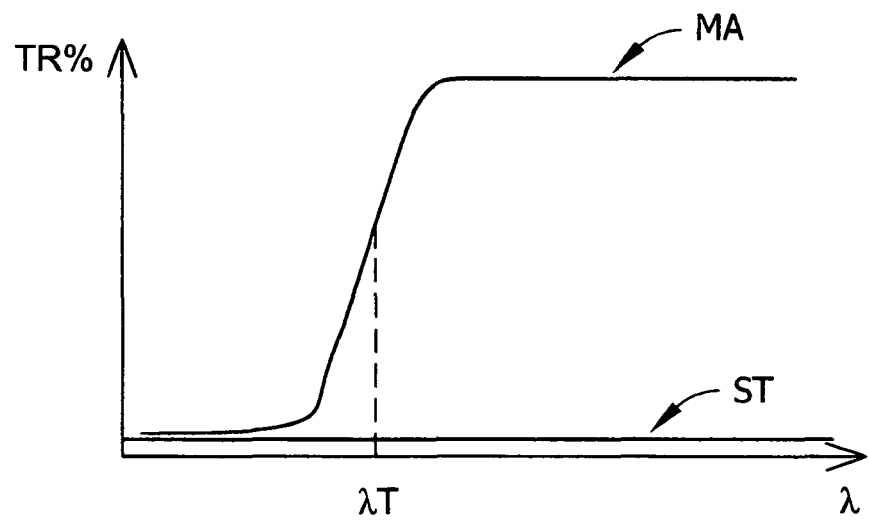
FIG. 3C shows transmission characteristics for materials (A) and (ST) in FIG. 1*a* which result in FIG. 1*b* operational characteristics.
Figure 3B:
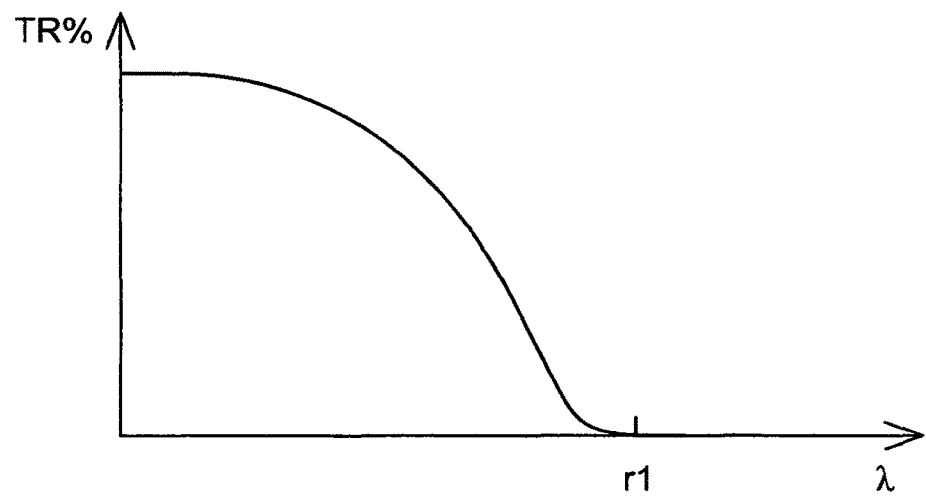
Figure 3C:
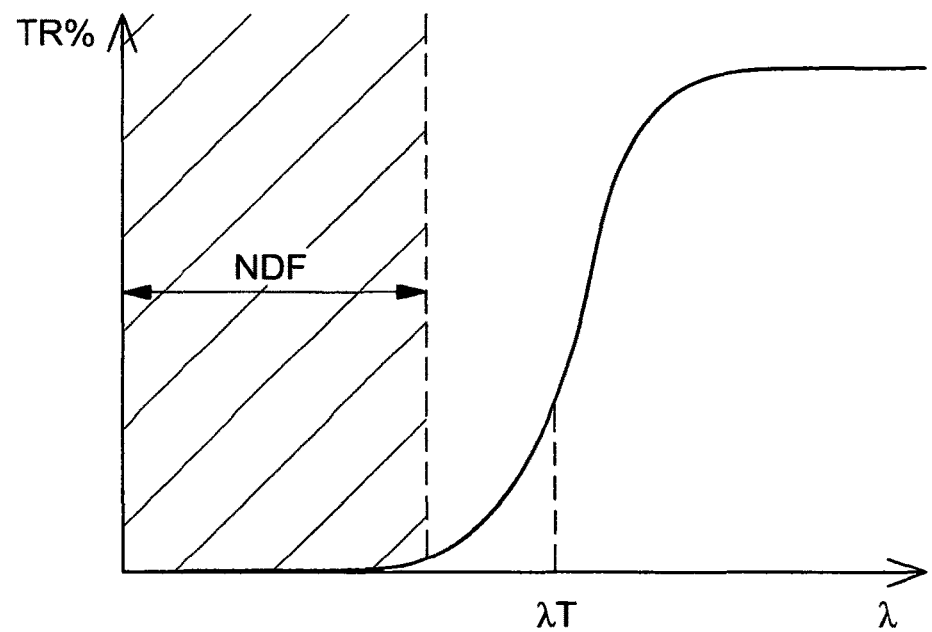

FIG. 3C shows transmission characteristics for material (A) and beam stopper (ST) in FIG. 3A1 which result in FIG. 3B operational characteristics. FIG. 3B shows that different wavelengths "see" a different aperture (AP) cross-sectional area, (eg. an opening radius varies between (r1) and (r2) with wavelength in an optimum operational design range). This is because of the wavelength dependent response of material (A). It will be appreciated that Figures like FIGS. 3B and 3C, but for a FIG. 3A2 embodiment also result, but with different Percent of Transmission (TR %) for the region between (r4) and (r2) based on the characteristics of material (ST). Any number of such Figures result based on the number of regions of different Materials, (eg. (MA), (Mb) and additional (Mc) etc.), and it is not believed necessary to show a multiplicity of embodiments in view of the examples provided by FIGS. 1A1, 1A2, 1B and 1C. However, FIG. 3B' is included to show a non-uniform optical density or thickness in filter characteristic in other than optimum wavelength range, (ie. beyond r1 in FIG. 3A1 is optimum and 0.0 to r1 is design non-optimum range), when transmission is greatest near the center of the filter. FIG. 3C' is included to show an enhanced neutral density filter (NDF) region of a said filter, indicating benefit can still obtain outside, (ie. to the left in FIG. 3C), of the design optimum operational wavelength range to the right thereof. FIGS. 3B' and 3C' focus on a primary benefit of the present invention, not previously disclosed.

FIG. 4A1 shows a side view of a Lens (L) with an aperture (AP) placed just therebefore. FIG. 4B1 shows a front view of said lens (L) and aperture (AP). As indicated by FIGS. 3A1-3C, the aperture (AP) diameter (D) varies with wavelength. FIGS. 4B2-4B5 show front views of various alternative lens shapes, namely square, rectangular, oval and elliptical. FIG. 4A2 shows that the lens (L) and aperture (AP) can be merged into an integrated embodiment. Both the FIG. 4A1 modular, and FIG. 4A2 integrated embodiments are disclosed as the Present Invention in this Disclose. FIG. 4A3 demonstrates that, for the purpose of this disclosure, a lens (L) can be, but need not be, a lens system comprising a plurality of elements, (eg. at least (LA) and (LB) elements). FIG. 4A3 also demonstrates that an aperture (AP) (AP') (AP") can alternatively be placed either before (AP) or after (AP') a Lens (LA), or between (AP") two elements (LA) (LB), or simultaneously at any selected multiple of said locations. This is the case regardless of the number of Lenses and Filters present. Note, FIG. 4A3 is not to be interpreted to imply that a lens system can not be comprised of more than two elements.

Figure 4C:
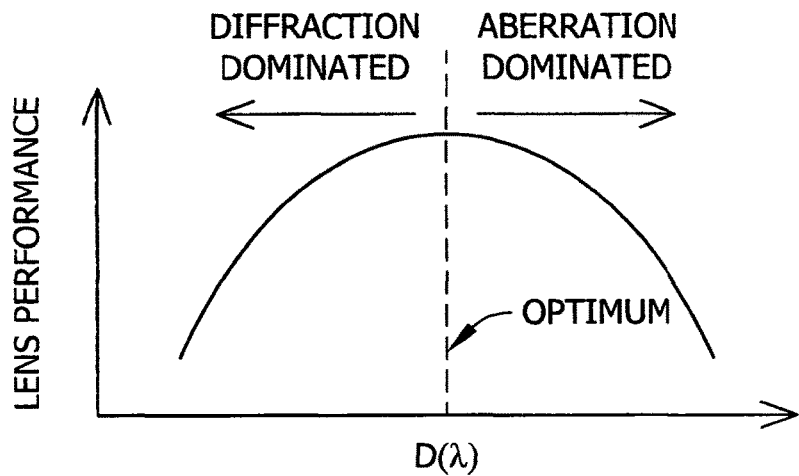
FIG. 4C shows the primary desired effect of the present invention.
Figure 5:
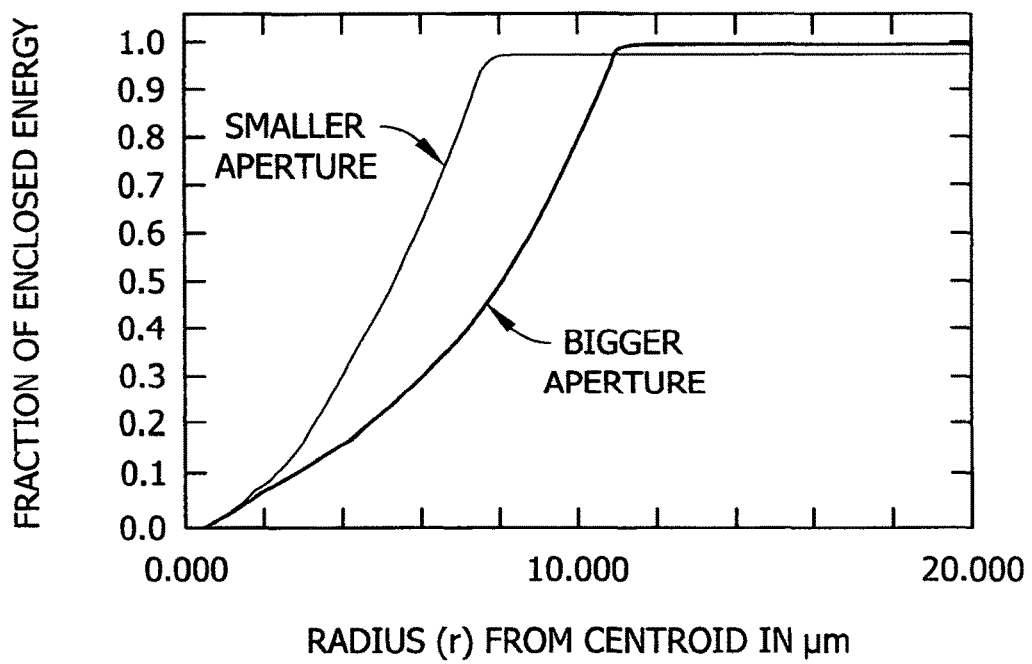

FIG. 4C shows the primary effect of a present invention system. Lens performance criteria is optimized in view of offsetting Wavelength dependent Aberration and Diffraction effects by Changing effective Diameter (D) of a beam. Larger or smaller diameters result in a less than optimum Lens Performance. FIG. 4C optimum design operational wavelength region is to the right therein. Very importantly, the Present Invention Claimed herein focuses applying such systems as represented by FIG. 4C in previously undisclosed "non-optimum" operational design wavelength regions, such as to the left in FIGS. 3B' and 3C' for example). This application has not been previously suggested.

FIG. 5 shows a plot of beam energy as a function of aperture (AP) radius (r).

Figure 6:
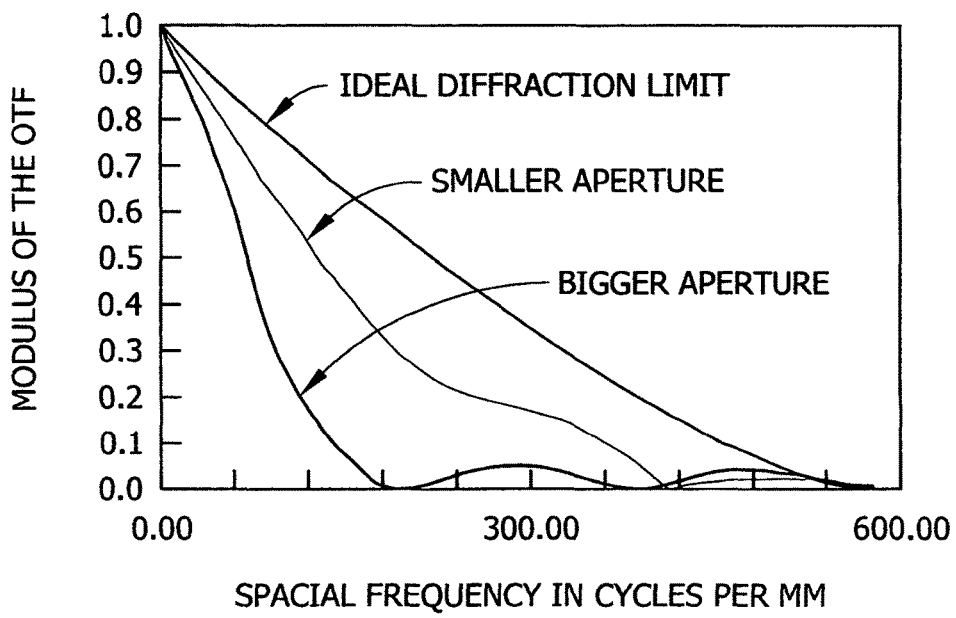
FIG. 6 demonstrates how aperture (PA) opening radius (r) affects resolution capability.

FIG. 6 demonstrates how aperture (AP) opening radius (r) affects resolution capability.

Figure 7:
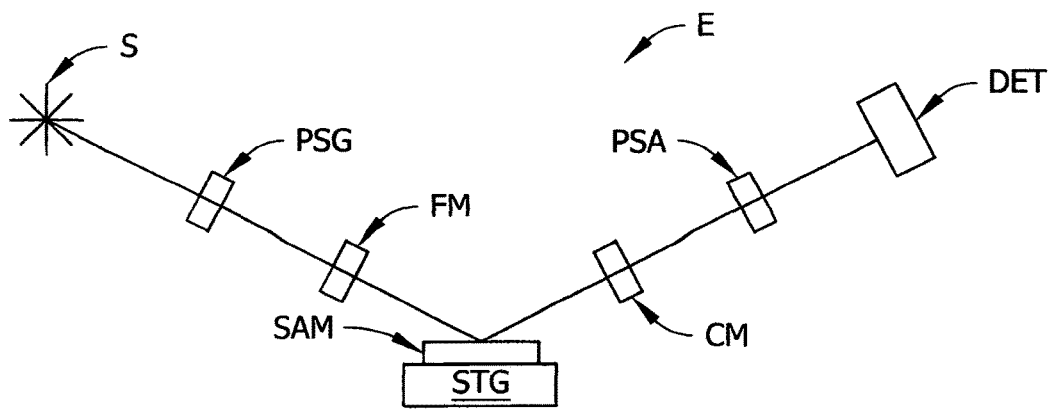
FIG. 7 demonstrates an ellipsometer and polarimeter (E) or the like system.

FIG. 7 demonstrates that an ellipsometer and polarimeter or the like system (E) generally comprises a source (S) of electromagnetic radiation, a polarization state generator (PSG), a stage (STG) for supporting a sample (SAM), a polarization state analyzer (PSA) and a data detector (DET). The polarization state generator (PSG) and polarization state analyzer (PSA) can each comprise a polarizer or analyzer respectively, and either can further comprise a compensator. Note that focusing (FM) and collimating (CM) are also shown. The present invention FIGS. 4A1 4A2 and 4A3 refractive lens (L) and aperture (A) (A') (A") can be applied at these locations.

Figure 8:
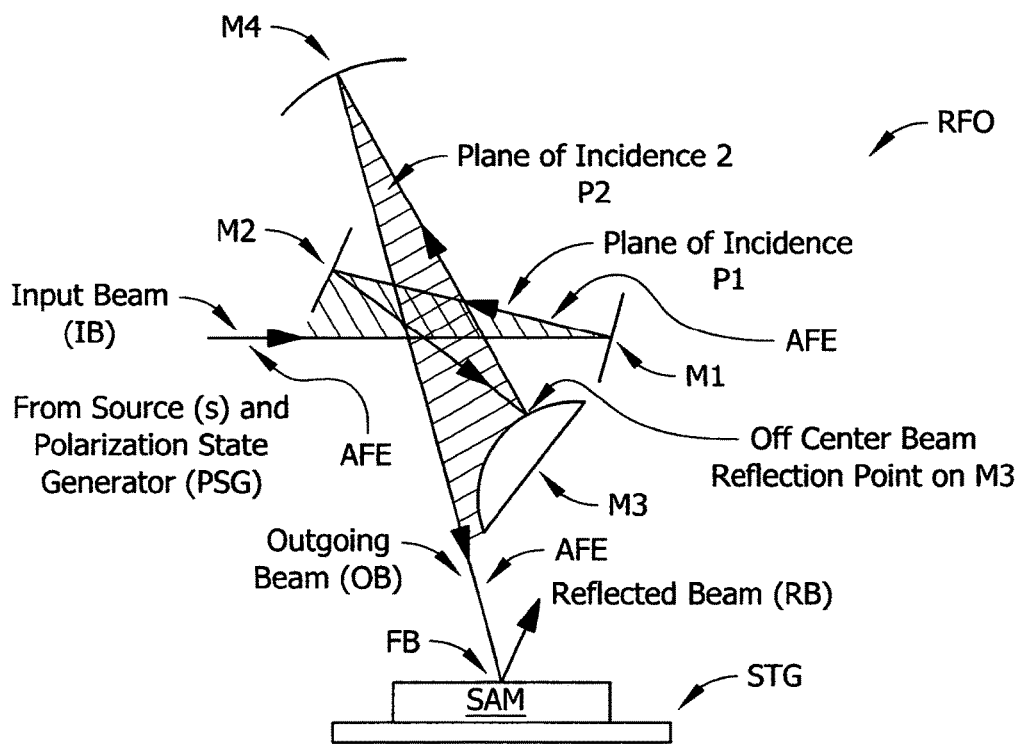
FIG. 8 is FIG. 1A1, with indication of where an additional filter element, and optionally an additional focusing element system can be positioned in the system for providing a focused beam (FB) of electromagnetic radiation onto a location on a sample (SAM).

FIG. 8 is FIG. 1A1, with indication of where an additional filter element, and and optionally focusing element can be positioned in the system for providing a focused beam (FB) of electromagnetic radiation onto a location on a sample (SAM). The preferred locations are indicated by "AFE". Note that the "F" can indicate only a Filter element, or a combination filter element and additional Focusing element.

It is noted that the terminology "naturally adjusted" as used in this Disclosure is to be interpreted to mean that a filter material optically responds to different wavelengths differently, so that an effective aperture diameter, and therefore the cross-sectional area of a beam of electromagnetic radiation interacting with an associated focusing element, is different for different wavelengths. The purpose being to provide a beam cross-sectional area which is more "optimum", optionally in view conflicting aberration and diffraction criteria, and therefore improve the operation of the focusing element.

Further, the terminology "Optimum" can mean, depending on context, that a Filter element provides an approximately best intensity level to a Reflective Optics system as a function of wavelength, or it can mean that an aperture size is adjusted to in view of an inherent tradeoff between diffraction and aberration effects in an associated refractive focusing element, as determined by an electromagnetic beam cross-sectional area for individual wavelengths, in said range of a multiplicity of wavelengths.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A system for providing a focused beam (FB) of electromagnetic radiation onto a location on a sample (SAM), said system being a reflective optics system (RFO) sequentially comprising first (M1), second (M2), third (M3) and fourth (M4) mirrors, each of said four mirrors (M1) (M2) (M3 (M4) providing reflective surfaces, with said third (M3) and fourth (M4) mirrors providing convex and concave reflective surfaces, respectively;

such that in use an input beam (IB) of electromagnetic radiation having a specific polarization state is directed toward said first (M1) mirror and reflects from said reflective surface thereof, such that a first plane of incidence (P1) is formed between said incident beam (IB) and said beam which is reflected from said reflective surface of said first (M1) mirror;

and such that said beam reflected from the reflective surface of said first (M1) mirror is directed toward said second mirror (M2) and reflects from said reflective surface thereof toward said convex third (M3) mirror, from which it reflects at an off-center location thereon toward said concave fourth (M4) mirror, wherefrom it is reflected by the reflective surface thereof toward said sample (SAM) as a focused (FB) outgoing beam (OB); said beam reflected from the reflective surface of said convex third (M3) mirror and that reflected from said reflective surface of said concave fourth (M4) mirror forming a second plane of incidence (P2), said first (P1) and second (P2) planes of incidence being substantially orthogonal to one another;

the effect of said four reflections from said reflective surfaces of said four (M1) (M2) (M3) (M4) mirrors being to substantially minimize the effects of all said reflections on the specific polarization state of said input beam, and to direct said output beam (OB) and provide it as a focused beam (FB) onto said sample (SAM) at the point it impinges thereupon;

said system further comprising a filtering element (AP) for naturally adjusting the effective cross-sectional area of a transmitted beam of electromagnetic radiation, as a function of wavelength;

said filtering element being present at a location selected from the group consisting of:
before mirror (M1);
between mirrors (M1) and (M2);
after mirror (M2).

2. A system as in claim 1, in which the first (M1) and second (M2) mirrors have flat reflecting surfaces.

3. A system as in claim 1, in which at least one of the first (M1) and second (M2) mirrors has a non-flat reflecting surface.

4. A system as in claim 1, in which both the first (M1) and second (M2) mirrors have non-flat reflecting surfaces.

5. A system as in claim 1, in which the input beam (IB), all reflected beams and the output beam (OB) are spectroscopic.

6. A system as in claim 1 in which the first (P1) and second (P2) planes of incidence are defined by central rays in the reflected beams involved.

7. A system as in claim 1 in which the input (IB), and the various reflected and output (OB) beams are each considered to consist of at least sixteen cross-sectional areas, and in which the calculated overall effect on polarization state of the various reflections from mirrors (M1) (M2) (M3) and (M4) is arrived at by an averaging thereof.

8. A system as in claim 1 in which the angles of incidence of the electromagnetic beams approaching said third (M3) and fourth (M4) mirrors are set to θ1 and θ2 degrees respectively, and in which the angles of incidence of the electromagnetic beams approaching said first (M1) and second (M2) mirrors are each selected from the group consisting of:
a) less than (θ1+θ2)/2;
b) (θ1+θ2)/2 degrees; and
c) greater that (θ1+θ2)/2 degrees.

9. A system as in claim 1 in which is made a selection from the group consisting of:
said mirrors (M1), (M2), (M3) and (M4) are substantially of the same substrate material; and
at least one of the mirrors (M1), (M2), (M3) and (M4) comprises substrate of one material and a coating thereupon of at least one different material.

10. A method as in claim 1, in which said filtering element is at least partially transmissive outside said range of wavelengths so that it provides a selection from the group of:
it provides a neutral density filter characteristic; and
it provides a gradient of transmissive characteristics such that optical density and/or thickness is substantially greater, or smaller, centrally in said filter and decreases or increases radially, respectively, outside said range of a multiplicity thereof wherein performance of said focusing element is rendered approximately optimum.

11. A system as in claim 1, wherein the filtering element absorbs electromagnetic radiation of some wavelengths but not others.

12. A system as in claim 1, wherein the filtering element reflects electromagnetic radiation of some wavelengths but not others.

13. A system as in claim 1, wherein the filtering element scatters electromagnetic radiation of some wavelengths but not others.

14. A system as in claim 1, wherein the filtering element performs at least two selections from the group consisting of:
it passes;
it reflects;
it scatters;
electromagnetic radiation of some wavelengths but not others.

15. A system as in claim 1, wherein, for each wavelength, focusing element aberration effects are substantially constant over a range thereof.

16. A system as in claim 1, wherein, for each wavelength, focusing element diffraction effects are substantially constant over a range thereof.

17. A system as in claim 1 wherein the effective cross-sectional area of a beam of electromagnetic radiation directed thereto, is naturally adjusted by said filtering element to be approximately optimum.

18. A system as in claim 1, wherein the cross-sectional area is of a shape selected from the group consisting of:
circular;
square;
rectangular;
oval; and
elliptical.

19. A system as in claim 1, wherein the focusing element and filtering element comprise a modular system of lenses and a modular filtering element.

20. A system as in claim 1, wherein the focusing element and filtering element comprise an integrated system of lenses and filtering element.

21. A system as in claim 1, wherein the focusing element and filtering element comprise a modular lens system comprising at least two modular lens elements and at least one modular filtering element positioned at a location selected from the group:
 before a lens element;
 after a lens element;
 between said at least two lens elements.

22. A system as in claim 1, wherein the focusing element and filtering element comprise a modular lens system comprising at least two modular lens elements and at least one filtering element integrated into at least one of said lens elements at a location selected from the group:
 before said lens element;
 after said lens element.

23. A system as in claim 22, wherein the focusing element and filtering element comprise a modular lens system comprising at least two modular lens elements, and at least one filtering element integrated into both lens elements, each thereof being at a location selected from the group:
 before said lens element;
 after said lens element.

24. A system as in claim 1, wherein the filtering element is of a constant thickness over its area.

25. A system as in claim 1, wherein the filtering element thickness is not a constant over its area.

26. A system as in claim 1, wherein the filtering element comprises at least two concentric regions of different materials, wherein a first material is present between a first effective radius and a second greater radius, and a second material is present between said second radius and a third even greater effective radius, all centered about a common origin.

27. A system as in claim 1, in which said system further comprises an additional focusing element in functional combination with said filtering element, in either order:
 a) said additional focusing element for focusing an electromagnetic beam, selected from the group consisting of:
  a lens (L); and
  a lens system comprising at least two elements (LA) (LB); and
 b) said filtering element (AP) for naturally adjusting the effective cross-sectional area of a transmitted beam of electromagnetic radiation, as a function of wavelength;
said focusing element (L) (LA) (LB) and said filtering element (AP) being functionally associated;
wherein the design criteria of said filtering element (AP) is that the effective cross-sectional area of the electromagnetic beam passed by said filtering element (AP) to said focusing element (L) (LA) (LB) is naturally adjusted with respect to wavelength for each wavelength in a range of a multiplicity thereof, such that the performance of the focusing element (L) (LA) (LB) is rendered approximately optimum in view of an inherent tradeoff between diffraction and aberration effects as a function of electromagnetic beam cross-sectional area in said range of a multiplicity of wavelengths;
said additional focusing element system being in functional combination with said filtering element and present at said selection from the group consisting of:
 before mirror (M1);
 between mirrors (M1) and (M2);
 after mirror (M2).

28. An ellipsometer comprising:
 a) a source of a beam of electromagnetic radiation;
 b) a polarization state generator;
 c) a reflective focusing optics system comprising:
  a system for providing a focused beam (FB) of electromagnetic radiation onto a location on a sample (SAM), said system being a reflective optics system (RFO) sequentially comprising first (M1), second (M2), third (M3) and fourth (M4) mirrors, each of said four mirrors (M1) (M2) (M3 (M4) providing reflective surfaces, with said third (M3) and fourth (M4) mirrors providing convex and concave reflective surfaces, respectively;
  such that in use an input beam (IB) of electromagnetic radiation having a specific polarization state is directed toward said first (M1) mirror and reflects from said reflective surface thereof, such that a first plane of incidence (P1) is formed between said incident beam (IB) and said beam which is reflected from said reflective surface of said first (M1) mirror;
  and such that said beam reflected from the reflective surface of said first (M1) mirror is directed toward said second mirror (M2) and reflects from said reflective surface thereof toward said convex third (M3) mirror, from which it reflects at an off-center location thereon toward said concave fourth (M4) mirror, wherefrom it is reflected by the reflective surface thereof toward said sample (SAM) as a focused (FB) outgoing beam (OB); said beam reflected from the reflective surface of said convex third (M3) mirror and that reflected from said reflective surface of said concave fourth (M4) mirror forming a second plane of incidence (P2), said first (P1) and second (P2) planes of incidence being orthogonal to one another;
  the effect of said four reflections from said reflective surfaces of said four (M1) (M2) (M3) (M4) mirrors being to substantially minimize the effects of all said reflections on the specific polarization state of said input beam, and to direct said output beam (OB) and provide it as a focused beam (FB) onto said sample (SAM) at the point it impinges thereupon;
 d) a stage (STG) for supporting a sample (SAM); and
 e) a polarization state detector (PSD);
  said system further comprising a filtering element (AP) for naturally adjusting the effective cross-sectional area of a transmitted beam of electromagnetic radiation, as a function of wavelength;
said filtering element being present at a location selected from the group consisting of:
 before mirror (M1);
 between mirrors (M1) and (M2);
 after mirror (M2).

29. A system as in claim 28, in which at least one of the first (M1) and second (M2) mirrors has a non-flat reflecting surface.

30. A system as in claim 28, in which both the first (M1) and second (M2) mirrors have non-flat reflecting surfaces.

31. A system as in claim 28, in which the input beam (IB), all reflected beams and the output beam (OB) are spectroscopic.

32. A system as in claim 28, in which the first (21) and second (P2) planes of incidence are defined by central rays in the reflected beams involved.

33. A system as in claim 28, in which the input (IB), and the various reflected and output (OB) beams are each considered to consist of at least sixteen cross-sectional areas, and in which the calculated overall effect on polarization state of the various reflections from mirrors (M1) (M2) (M3) and (M4) is arrived at by an averaging thereof.

34. A system as in claim 28, in which the angles of incidence of the electromagnetic beams approaching said third (M3) and fourth (M4) mirrors are set to θ1 and θ2 degrees respectively, and in which the angles of incidence of the electromagnetic beams approaching said first (M1) and second (M2) mirrors are each selected from the group consisting of:
- a) less than (θ1+θ2)/2;
- b) (θ1+θ2)/2 degrees; and
- c) greater that (θ1+θ2)/2 degrees.

35. A system as in claim 28 in which is made a selection from the group consisting of:
- said mirrors (M1), (M2), (M3) and (M4) are substantially of the same substrate material; and
- at least one of the mirrors (M1), (M2), (M3) and (M4) comprises substrate of one material and a coating thereupon of at least one different material.

36. A system as in claim 28 which further comprises additional fifth (M1'), sixth (M2'), seventh (M3') and eighth (M4') mirrors arranged in a substantially mirror image with respect to mirrors (M1), (M2), (M3) and (M4), said mirrors (M1'), (M2'), (M3') and (M4') serving to and direct said beam into a polarization state detector (PSD).

37. A method as in claim 36, in which mirrors (M3) and (M3') are convex and the beam of electromagnetic radiation reflecting therefrom is from an off-center location thereupon.

38. An ellipsometer system as in claim 28, in which said system further comprises an additional focusing element in functional combination with said filtering element, in either order:

a) said additional focusing element for focusing an electromagnetic beam, selected from the group consisting of:
- a lens (L); and
- a lens system comprising at least two elements (LA) (LB); and b) said filtering element (AP) for naturally adjusting the effective cross-sectional area of a transmitted beam of electromagnetic radiation, as a function of wavelength;

said focusing element (L) (LA) (LB) and said filtering element (AP) being functionally associated;

wherein the design criteria of said filtering element (AP) is that the effective cross-sectional area of the electromagnetic beam passed by said filtering element (AP) to said focusing element (L) (LA) (LB) is naturally adjusted with respect to wavelength for each wavelength in a range of a multiplicity thereof, such that the performance of the focusing element (L) (LA) (LB) is rendered approximately optimum in view of an inherent tradeoff between diffraction and aberration effects as a function of electromagnetic beam cross-sectional area in said range of a multiplicity of wavelengths;

said additional focusing element system being in functional combination with said filtering element and present at said selection from the group consisting of:

before mirror (M1);

between mirrors (M1) and (M2);

after mirror (M2).

\* \* \* \* \*